(12) United States Patent
Youngman et al.

(10) Patent No.: US 6,664,074 B2
(45) Date of Patent: Dec. 16, 2003

(54) USE OF YACM AND YQEJ, ESSENTIAL BACTERIAL GENES AND POLYPEPTIDES AND THEIR USE

(75) Inventors: Philip Youngman, Boston, MA (US); Christian Fritz, Natick, MA (US); Luz-Maria Guzman, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/792,251

(22) Filed: Feb. 23, 2001

(65) Prior Publication Data

US 2002/0160364 A1 Oct. 31, 2002

(51) Int. Cl.[7] .............................. C12Q 1/18; C12Q 1/68; G01N 33/53; A61K 38/00; C12N 1/20

(52) U.S. Cl. .............................. 435/32; 435/6; 435/7.1; 435/252.3; 514/12; 514/14

(58) Field of Search .......................... 435/6, 252.3, 7.1, 435/32; 514/12, 44

(56) References Cited

U.S. PATENT DOCUMENTS 6,187,541 B1    2/2001    Benton et al. ............... 435/6

OTHER PUBLICATIONS

Blattner, F., "The Complete Genome Sequence of *Escherichia coli* K–12", *Science*, vol. 277, pp. 1453–1475, Sep. 5, 1997.

Kuzuyama, T., "Formation of 4–(cytidine 5'diphospho)–2–C–methyl–D–erythritol from 2–C–methyl–D–erythritol 4–phosphate cytidylyltransferase, a new enzyme in the nonmevalonate pathway", *Tetrahedron Letters*, vol. 41, No. 5, pp. 703–706, Jan. 29, 2000.

Mehl, R., "Identification of the *Escherichia coli* Nicotinic Acid Mononucleotide Adenylyltransferase Gene", *Journal of Bacteriology*, vol. 182, No. 15, pp. 4372–4374, Aug. 2000.

Ogasawara, N., "Systematic Sequencing of the 180 Kilobase Region of the *Bacillus Subtilis* Chromosome Containing the Replication Origin", *DNA Research*, vol. 1 , pp. 1–14, 1994.

Oshima, T., "A 718–kb DNA Sequence of the *Escherichia coli* K–12 Genome Corresponding to the 12.7–28.0 min Region on the Linkage Map", *DNA Research*, vol. 3, pp. 137–155, 1996.

Rohdich, F., "Cytidine 5'–triphosphate–dependent biosynthesis of isoprenoids: YgbP protien of *Escherichia coli* catalyzes the formation of 4–diphosphocytidyl–2–C– methylerythritol", *Proceedings of the National Academy of Sciences of the United States of America*, vol. 96, No. 21, pp. 11689–11210, Oct. 12, 1999.

Chen, X., et al., "TTD: Therapeutic Target Database." *Nucleic Acid Research*. vol. 30, No. 1, pp. 412–415, 2002.

Gerdes, S.Y., et al. "From Genetic Foodprinting to Antimicrobial Drug Targets: Examples in Cofactor Biosyntheic Pathways." *Journal of Bacteriology*, vol. 184, No. 16, pp. 4555–4572, Aug. 2002.

Moir, D.T., et al., "Genomic and Antimicrobial Drug Discovery." *Antimicrobial Agents and Chemotherapy*, vol. 43, No. 3, pp. 439–446, Mar. 1999.

O'Neill, A.J., et al. "Letters to the Editor: Use of Mutator Strains for Characterization of Novel Antimicrobial Agents." *Antimicrobial Agents and Chemotherapy*, vol. 45, No. 5, pp. 1599–1560, May 2001.

*Primary Examiner*—Rodney P Swartz
*Assistant Examiner*—Khatol S Shahnan-Shah
(74) *Attorney, Agent, or Firm*—Fish & Richardson P.C.

(57) ABSTRACT

Disclosed are genes, termed "yacM" and "yqeJ," which are essential for survival for a wide range of bacteria, such as *Streptococcus pneumoniae, Bacillus subtilis,* and *E. coli.* These genes and the essential polypeptides they encode can be used to identify antibacterial agents for treating a broad spectrum of bacterial infections.

8 Claims, 8 Drawing Sheets

Streptococcus pneumoniae "yacM": STRPN_yacM_orf STRPN_MPI_Contig394 1875-2582 strand(-) (single base correction based on trace of san001G038g10f1)

```
  1 ATGATTTATGCAGGAATTCTTGCCGGTGGAACTGGCCACACGGGATCAGTAGCTGCCAAAACAATTTTAGAGCTAGGTGATCGACCTATTTTGA  100
    TACTAAATACGTCCTTAAGAACGGCCACCTTGACCGTGCCAGTCATTCGAATCGATCCACTAGCTGGATAAAACT
  1 M  I  Y  A  G  I  L  A  G  G  T  G  T  R  M  G  I  S  N  L  P  K  Q  F  L  E  L  G  D  R  P  I  L  I    34

101 TTCATACAATTGAAAAATTGTCTTGGAGCCAAGTATTGAAAAAATTGTAGTGGTTCATGGAGACTGGGTTTCTCATGCAGAGATCTTGTAGATAA  200
    AAGTATGTTAACTTTTTAACAGAACCTCGGTTCATAACTTTTTAACATCAACCACAAGTACCTCTGACCCAAAGAGTACGTCTCTAGAACATCTATT
 35 H  T  I  E  K  F  V  L  E  P  S  I  E  K  I  V  V  G  V  H  G  D  W  V  S  H  A  E  D  L  V  D  K    67

201 ATATCTCCTCTTTATAGGAACGTATCATCATTACAAAGGTGGTCTGACCGCAATCACAGTATTAAGAACATCATTGAAGCCATTGATGCTTATCGT  300
    TATAGAGGAGAAATATTCCTTGCATAGTAGTAATGTTTCCACCAGACTGGCGTTATGTTCATAATTCTTGTAGTAACTTCGGTAACTACGAATAGCA
 68 Y  L  P  L  Y  K  E  R  I  I  I  T  K  G  G  A  D  R  N  T  S  I  K  N  I  I  E  A  I  D  A  Y  R    100

301 CCGCTTACTCCAGGAGGATATCGTTGTTACCCAGATTCTCGTTCGTCCATTATTACACTTCGATGATTCAGGACAATATCCAACTTGCCAAAATCATG  400
    GGCGAATGAGGTCCTATAGCAACAATGGGTGCTAAGACAGCAGTTCAGAGGCTACTAAGTCCTGTTATAGGTTGAACGGGTTTAGTAC
101 P  L  T  P  E  D  I  V  V  T  H  D  S  V  R  P  F  F  I  T  L  R  M  I  Q  D  N  I  Q  L  A  Q  N  H  D  134

401 ACGCAGTGGACACAGTGGTAGAAGCGGTTGATACTATCGTTGAAGTACCAATGGTCAATTTATTACAGATATTCAAATCGTCTCACCTTTATCAAGG  500
    TGCGTCACCTGTGTCACCATCTTCGCCAACTATGATAGCAACTTCATGGTTACCAGTTAAATAATGTCTATAAGGTTTAGCACGAGTGGAAATAGTCC
135 A  V  D  T  V  V  E  A  V  D  T  I  V  E  S  T  N  G  Q  F  I  T  D  I  P  N  R  A  H  L  Y  Q  G    167

501 ACAAACACCTCAAACATTCCGTGCAAGGACTTCATGACTTCTTTCTGATGAAGAGAAATCTTGACAGATGCATGTAAAATCTTT  600
    TGTTTGTGGAGTTTGTAAGGCAACGTTCCTGAAGTACTGAAGACTACTTCTCTTCCTTTAGAACTGTCTACGTACATTTTAGAAA
168 Q  T  P  Q  T  F  R  C  K  D  F  M  D  L  Y  G  S  L  S  D  E  E  K  E  I  L  T  D  A  C  K  I  F    200

601 GTGATCAAAGGAAAAGATGGCTTTGGCCAAAGTGAATACTCAAATCTGAAGATTACAACCGTAACGATTGAAGATTTGAAGATTCAAAAGTATGATTGAGA  700
    CACTAGTTTCCTTTTCTACCGAAACCGGTTTCACTTAGACTTCTAAGTTTGAGTTGCATTGCTAAAGTTCTAAACTCTAACTCT
201 V  I  K  G  K  D  V  A  L  A  K  G  E  Y  S  N  L  K  I  T  T  V  T  D  L  K  I  A  K  S  M  I  E  K    234

701 AAGACTAG  708              (SEQ ID NO: 1)
    TTCTGATC                   (SEQ ID NO: 3)
235 D  *    236                (SEQ ID NO: 2)
```

FIG. 1

Streptococcus pneumoniae "yqeJ": STRPN_yqeJ_orf STRPN_MPI_Contig617 3936-4555 strand(-)
(note possible alternative translation start at position 40 (TTG) of reported sequence)

```
  1 ATGACAATCGAACTATTGACTCCCTTTACCAAGTAGAGTTGGAGCCAGAAATCAAGGAGAAAAACGCAAACAAGTTGGATTTTAGGGGGAATTTTA 100
    TACTGTTAGCTTGATAACTGAGGGAAATGTTCCATCTCAACTCGGTCTTTAGTTCCTCTTTTTTTGCGTTTGTTCAACCTAAAATCCCCCCTTAAAAT
  1 M  T  I  E  L  L  T  P  F  T  K  V  E  L  E  P  E  I  K  E  K  K  R  K  Q  V  G  I  L  G  G  N  F  N  34

101 ACCCTGTTCACAATGCCCATCTCATTGTTGCGGATCAAGTACGGCAACAGTTGGGACTGATCAAGTTCTTCTCATGCCTGAATACCAACCTCCTCACGT 200
    TGGGACAAGTGTTACGGGTAGAGTAACAACGCCTAGTTCATGCCGTTGTCAACCCTGACCTAGTTCAAGAAGAGTACGGACTTATGGTTGGAGGAGTGCA
 35 P  V  H  N  A  H  L  I  V  A  D  Q  V  R  Q  Q  L  G  L  D  Q  V  L  L  M  P  E  Y  Q  P  P  H  V  67

201 TGATAAAGGAAACCATCCCTGAACACCATCGTCTCAAGATGCTTGAGTTGGCAATTGAGGGGATTGACGGCCTAGTCATTGAACCATTGAGTTGGAG 300
    ACTATTTTCCTTTGGTAGGGACTTGTGGTAGCAGAGTTCTACGAGTTCTAAAACTGTCTCTTCTTAGGTCTATGCTAATATGAAATAGTAGCCTGTAACTCAACCTC
 68 D  K  K  E  T  I  P  E  H  H  R  L  K  M  L  E  L  A  I  E  G  I  D  G  L  V  I  E  T  I  E  L  E  100

301 CGCAAGGGTATTTCCTACACCTACGATACATGAAGATTTTGACAGAGAAGAATCCAGATACGATTATACTTTATCATCGGTGCCGACATGGTTGACT 400
    GCGTTCCATAAAGGATGTGGATGCTATGTACTTCTAAAACTGTCTCTTAGGTCTATGCTAATATGAAATAGTAGCCACGGCTGTACCAACTGA
101 R  K  G  I  S  Y  T  Y  D  T  M  K  I  L  T  E  K  N  P  D  T  D  Y  Y  F  I  I  G  A  D  M  V  D  Y  134

401 ATCTGCCTAAGTGTACCGAATTGATGAACTGGTTGACATGGTTCAGTTTGTGGGGGTTCAGCGTGCCACGCTACAAGGTAGGACTTCCTATCCAGTTAT 500
    TAGACGGATTCACATGGCTTAACTACTTGACCAACTGTACCAAGTCAAACACCCCAAGTGCGATGTTCCATCCTGAAGGATAGGTCAATA
135 L  P  K  W  Y  R  I  D  E  L  V  D  M  V  Q  F  V  G  V  Q  R  P  R  Y  K  V  G  T  S  Y  P  V  I  167

501 CTGGGTGGACGTACCGCTCATGATGATATCTCGTCCAGCATGGTGCCGGGACTTCCTGCCCAAGGTCGGAAACCAACTTCTCTACCTCAGCCAGTGCTA 600
    GACCCACCTGCATGGCGAGTGCGAGTACCTATAGAGCAGGTCGTACCACGCGTCCAGCTGTTCCAGCGTTGAAAGAGGAGGAGGTCACGAT
168 W  V  D  V  P  L  M  D  I  S  S  M  V  R  D  F  L  A  Q  G  R  K  P  N  F  L  L  P  Q  P  V  L  200

601 GACTACATCGAGAAGGAGGGGCTCTACTGA     630    (SEQ ID NO: 4)
    CTGATGTAGCTCTTCCTCCCGAGATGACT            (SEQ ID NO: 6)
                                             (SEQ ID NO: 5)
201 D  Y  I  E  K  E  G  L  Y  *    210
```

FIG. 2

```
Bacillus subtilis yacM: gi|2632267|gb|Z99104.1|BSUB0001 109786-110484 strand(+)
(position 1 of this sequence corresponds to position 109786 of gi:2632267)

1  ATGAGTTATGATGTGGTGATTCCTGCAGCCGGACAGGGAAAGCGGATGAAGGCAGGCGAATAAACTGTTCATTGAGCTGAAGGGAGACCCGGTGATCA  100
     TACTCAATACTACACCACTAAGGACGTCGGCCTGTCCCTTTCGCCTACTTCCGTCCGCTTATTTGACAGTAACTGACTTCCCTCTGGGCCACTAGT
  1   M  S  Y  D  V  V  I  P  A  A  G  Q  G  K  R  M  K  A  G  R  N  K  L  F  I  E  L  K  G  D  P  V  I  I   34
101  TACACACGTTAAGAGTGTTTGACAGCCACCGGACAGTGCGATAAAATCATTTTGGTGATTAACGAGCAGGAGCGGGAGCACTTTCAGCAATTGCTGTCCGA  200
     ATGTGTGCAATTCTCACAAACTGTCGGTGGCCGTCACCGTATTTTAGTAAACCACTATTGCTCGTCCTCCGCCCTCGTGAAAGTCGTTAACGACAGGCT
 35   H  T  L  R  V  F  D  S  H  R  Q  C  D  K  I  I  L  V  I  N  E  Q  E  R  E  H  F  Q  Q  L  L  S  D    67
201  TTACCCGTTTCAAACTTCAATTGAGCTTGTTGCAGGCGGAGATGAGCCACAGCACAGTGTGTATAAGGGCTGTGAAAGCCGTAAAGCAGGAAAAGATTGTC  300
     AATGGGCAAAGTTTGAAGTTAACTGCGACAACGTCCGCCTTCTCGGTGTCGTCACACATATTCCCGACACTTTCGGCATTTCGTCCTTTTCTAACAG
 68   Y  P  F  Q  T  S  I  E  L  V  A  G  G  D  E  R  Q  H  S  V  Y  K  G  L  K  A  V  K  Q  E  K  I  V    100
301  CTTGTACATGACGGTGCCCGTCCATTATAAAACATGAACAAATTGACGAACTGCAGAGGCGGAACAGGAGGAGGCCCATCCTTGCTTCCGG  400
     GAACATGTACTGCCACGGGCAGGTAATATTTGTTTAACTGCTTGTCAACATTTGTTCCTGCCGGTAGAACGACAAGGCC
101   L  V  H  D  G  A  R  P  F  F  I  K  H  E  Q  I  D  E  L  I  A  E  A  E  Q  T  G  A  A  I  L  A  V  P  V  134
401  TAAAAGATACGATTAAACGCGTTCAAGATTTACAAGTCAGTGAGACGATTGAACGTTCAGTCTCTGTTCAGTTCAAGTCTGCAACACCCGACAGGTTTGTCGGTGTTCGAAAAGCAGAAAG  500
     ATTTTCTATGCTAATTGCGCAAGTTCTAAATGTTCAGTCACTCAGACAAGTCAGAACAGAGACAAGTCAGAGACAGCCACAAGCTTTCGTCTTTC
135   K  D  T  I  K  R  V  Q  D  L  Q  V  S  E  T  I  E  R  S  S  L  W  A  V  Q  T  P  Q  A  F  R  L  S    167
501  TTTATTGATGAAGGCTCACGCTGCGAGCCGAGCGCCAAGGATTTTTAGGACGGATGACGCCAGCCTCGTTGAACAGATGGAGGGCGGTTCGGTCCGTGTT  600
     AAATAACTACTTCCGAGTGCGACTCCGGCTCGCGTTCCTAAAATCCCTGCCTACTGCGGTCGGAGCAACTTGTCTACCTCCCGCCAAGCAGGCACAA
168   L  L  M  K  A  H  A  E  A  E  R  K  G  F  L  G  T  D  D  A  S  L  V  E  Q  M  E  G  G  S  V  R  V    200
601  GTAGAAGGCAGCTATACAAATATTAAGCTGACGACGCCAGACGATTTGACGCTGACTTCAGCAGAGCTATCATGAATCAGAAAGTGGAATAACATGTTTAG  699
     CATCTTCCGTCGATATGTTTATAATTCGACTGCTGCTGAAACTGCAGTCGACTTCGATAGTACCTTAGTCTTTCACCCTATTGTACAAATC
201   V  E  G  S  Y  T  N  I  K  L  T  T  P  D  D  L  T  S  A  E  A  I  M  E  S  E  S  G  N  K  H  V  *   233

(SEQ ID NO: 7)
(SEQ ID NO: 9)
(SEQ ID NO: 8)
```

FIG. 3

```
Escherichia coli ygbP: gi|2367156|gb|AE000358.1|AE000358 6754-7464 strand(-)
(position 1 of this sequence corresponds to position 7464 of gi:2367156)

1 ATGGCAACCACTCATTTGGATGTTTGCGCCGTGGTTCCGGCGGCCGGATTTGGCCGTCGGATTGCCCGTCAAGCGAATGTCCTAAGCAATATCTCTCAATCGGTA  100
    TACCGTTGGTGAGTAACCTACAAACGCGGCACCAAGGCCGCCGCCGGCCTAAACGCGGCCTAAACGTCGCACGCAGCTTACGTTTGCCTTACAGGATTCGTTATAGAGACTTAGCCAT
  1  M  A  T  T  H  L  D  V  C  A  V  V  P  A  A  G  F  G  R  R  M  Q  T  E  C  P  K  Q  Y  L  S  I  G  N   34

101 ATCAAACCATTCTTGAACTCTGGTGCATGCGCGTCGCATCCCGGGAAACGTGTCGTCATTGCCATAAGTCCTGGCGATAGCCGTTTTGCACA                200
    TAGTTTGGTAAGAACTTGAGACCACGTACGCGCAGCGTAGGGCCCACTTGCACAGCAGTAACGTATTCAGGACCGTATCGGCAAAACGTGT
 35  Q  T  I  L  E  H  S  V  H  A  L  L  A  H  P  R  V  K  R  V  V  I  A  I  S  P  G  D  S  R  F  A  Q       67

201 ACTTCCTCTGGCAATCATCCGCAAATCACCGTTGTAGATGCGGTGATGAGCCGTGCCGATTCCGTCGGCAGGTCTGAAAGCCGCTGGCGACGCGCAG          300
    TGAAGGAGACCGTTAGTAGGCGTTAGTGGCAACATCTACCGCCACTACTCGCACGGCTAAGGCACGACGTCCAGACTTTCGGCGACCGCTGCCGTC
 68  L  P  L  A  N  H  P  Q  I  T  V  V  D  G  G  D  E  R  A  D  S  V  L  A  G  L  K  A  A  G  D  A  Q     100

301 TGGGTATTGGTGCATGACGCGCGCTCGTCCTTGTTGCATCAGGATGACCTCGCGCAGTTGTTGGCGTTGAGCGAAGAACCAGCCGACGCGCGGGGGATCCTCG    400
    ACCCATAACCACGTACTGCGCGCGAGCAGGAACAAACGTAGTCCTACTGGAGCGCGTCAACACCGCTAACCCAACTCGTTTGTTGGTCGGCTGCCCCCCTAGGAGC
101  W  V  L  V  H  D  A  A  R  P  C  L  H  Q  D  D  L  A  R  L  L  A  L  S  E  T  S  R  T  G  G  I  L  A   134

401 CCGCACCAGTGCGCGATACTATGAAACGTGCCGAACCGGGCAAAAATGCCATTGCCGTTGATCGCAACGGCTTATGGCACGGCCTGACGCCGCA              500
    GGCGTGGTCACGCGCTATGATACTTTGCACGGCTTGGCCCGTTTTACGGTAACGATAGCGTCAACCTAGCGTTGCCGAATACCGTGCCGACTGCGGCGT
135  A  P  V  R  D  T  M  K  R  A  E  P  G  K  N  A  I  A  H  T  V  D  R  N  G  L  W  H  A  L  T  P  Q     167

501 ATTTTTCCCTCGTGAGCTGTTACATGACTGTCTGACGCGCGCTCAAATGAAGGCCGACTATTACCGACGAAGCCTCGGCGCTGGAATATTGCGATTC         600
    TAAAAAGGGAGCACTGACAATGTACTGACAGACTGCGCGCGAGATTTACTTCCGGCTGATAATGCCTGCTTCGGAGCCGCGACCTTATAACGCCTAAG
168  F  F  P  R  E  L  L  H  D  C  L  T  R  A  L  N  E  G  A  T  I  T  D  E  A  S  A  L  E  Y  C  G  F     200

601 CATCCTCAGTTGGTCGAAGGCCGTGCGGATAACATTAAGGTCACGCGCCCGGAAGATTTGGCACTGGCCGAGTTTTACCTCACCGAACCATCCATCAGG        700
    GTAGGAGTCAACCAGCTTCCGGCACGCCTATTGTAATTTCAGTGCGCGGGCCTTCTAAACCGTGACCGGCTCAAATGGAGTGGCGTTGGTAGTAGTCC
201  H  P  Q  L  V  E  G  R  A  D  N  I  K  V  T  R  P  E  D  L  A  L  A  E  F  Y  L  T  R  T  I  H  Q  E   234

701 AGAATACATAA  711       (SEQ ID NO: 10)
    TCTTATGTATT          (SEQ ID NO: 12)
235  N  T  *      237    (SEQ ID NO: 11)
```

FIG. 4

```
Bacillus subtilis yqeJ: gi|2634966|gb|Z99117.1|BSUB0014 43581-44150 strand(-)
(position 1 of this sequence corresponds to position 44150 of gi:2634966)

1  ATGAAGAAAATCGGAATTTTCGGAGGCACGTTTGACCCTCCGCATAATGGTCACCTCTTAATGGCGAATGAGGTTGCTGTGTACCAGGCGGGGCTTGATGAAA    100
     TACTTCTTTGCCTTAAAAGCCTCCGTGCAAACTGGGAGGCGTATTACCAGTGGAGAATTACCGTTACTCCACGACATGGTCCGCCCCGAACTACTTT
  1  M  K  K  I  G  I  F  G  G  T  F  D  P  P  H  N  G  H  L  L  M  A  N  E  V  L  Y  Q  A  G  L  D  E  I     34

101  TTTGGTTTATGCCTAATCAAATTCCGCCGCATAAACAGAACGAAGACTATACCGACAGTTTCATCGCGTGGAAATGCTAAAGCTTGCAATTCAATCTAA    200
     AAACCAAATACGGATTAGTTTAAGGCGGCGTATTTGTCTTGCTTCTGATATGGCTGTCAAAGTAGCCACCTTTACGAATTCGAACGTTAAGTTAGATT
 35  W  F  M  P  N  Q  I  P  P  H  K  Q  N  E  D  Y  T  D  S  F  H  R  V  E  M  L  K  L  A  I  Q  S  N      67

201  TCCGTCCTTAAGCTGGAGCTTGTTGAAATGGAAAGAGAAGGGCCATCATATACCTTTGATACCGTTTCTTACTGAAGCAGCGTTATCCAATGATCAG    300
     AGGCAGGAATTCGACCTCGAACAACTTTACCTTCTCTTCCCGGTAGTATATGGAAACTATGGCAAACTTCGTCGCAATAGTTTACTAGTC
 68  P  S  F  K  L  E  L  V  E  M  E  R  E  G  P  S  Y  T  F  D  T  V  S  L  L  K  Q  R  Y  P  N  D  Q     100

301  CTGTTCTTTATTATCGGCGCTGATATGATTGAATATTTGCCGAAATGGTATAAGCTTGACGAGCTGCTGAACCTCATTCAATTTATTGGAGTAAAGCGCC    400
     GACAAGAATAATAGCCGCGACTACTAATACTTATAAACGGCTTTACCATATTCGACCTGCTGGAGTAAGTTAAATAACCTCATTTCGCGG
101  L  F  F  I  I  G  A  D  M  I  E  Y  L  P  K  W  Y  K  L  D  E  L  L  N  L  I  Q  F  I  G  V  K  R  P    134

401  CCGGTTTTCATGTTGAAACCCCCTATCCGCTTCTCTTTGCAGACGTTCCGGAATTTGAGGTATCATCAACTATGATAAGGGAACGGTTTAAAAGCAAGAA    500
     GGCCAAAAGTACAACTTTGGGGAATAGGCGAAGAGAAACGTCTGCAAGGCCTTAAACTCCATAGTAGTTGATACTATTCCCTTGCCAAATTTTCGTTCTT
135  G  F  H  V  E  T  P  Y  P  L  L  F  A  D  V  P  E  F  E  V  S  S  T  M  I  R  E  R  F  K  S  K  K     167

501  GCCCACTGACTACTTAATCCCTGATAAAGTGAAGAAGTATGTAGAGGAGAATGGTTTATATGAATCGTGA   570    (SEQ ID NO: 13)
     CGGGTGACTGATGAATTAGGGACTATTTCACTTCTTCACATCCTCCTCTTACCAAATATACTTAGCACT          (SEQ ID NO: 15)
168  P  T  D  Y  L  I  P  D  K  V  K  K  Y  V  E  E  N  G  L  Y  E  S  *    190    (SEQ ID NO: 14)
```

FIG. 5

Escherichia coli ybeN: gi|1786849|gb|AE000168.1|AE000168 7666-8307 strand(-)
(position 1 of this sequence corresponds to position 8307 of gi:1786849)

```
  1 ATGAAATCTTTACAGGCTCTCTTTGGCGGCACCTTTGATCCGGTGCACTATGGTCATCTAAAACCCGTGGAAATTTGATTGGTCTGACGC    100
    TACTTTAGAAATGTCCGAGACAAACCGCCGTGGAAACTAGGCCACGTGATACCAGTAGATTTTGGGCACCGCTTAAACTAACCAGACTGCG
  1  M  K  S  L  Q  A  L  F  G  G  T  F  D  P  V  H  Y  G  H  L  K  P  V  E  T  L  A  N  L  I  G  L  T  R     34

101 GGGTCACAATCATCCCTAATAATGTTCCTCCGCATCGTCCCCAGCCGGAAGCGAACAGCGTGCAGCGTAAACACATGCTTGAACTGGCCGACAA    200
    CCCAGTGTTAGTAGGGATTATTACAAGGAGGCGTAGCAGGGGTCGGCCTTCGCGCTTGTGCACGTCGCATTTGTGTACGAACTTGACCGGCTGTT
 35  V  T  I  I  P  N  N  V  P  P  H  R  P  Q  P  E  A  N  S  V  Q  R  K  H  M  L  E  L  A  I  A  D  K     67

201 GCCATTATTATTCTTGATGAACGCGAGCTAAAGCGCAATGCCCCTCTTACACTGCGCAAACACTGAAAGAGTGGCGGCAGGAACAAGGACCGACGTG    300
    CGGTAATAATAAGAACTACTTGCGCTCGATTTCGCGTTACGGGGAGAATGTGACGCGTTTGACTTTCTCACCGCCGTCCTTGTTCCTGGCCTGCAC
 68  P  L  F  T  L  D  E  R  E  L  K  R  N  A  P  S  Y  T  A  Q  T  L  K  E  W  R  Q  E  Q  G  P  D  V    100

301 CCGCTGGCGTTTATTATTGGTCAGGATTCACTGCTGACCTTTCCGACCTGGTACGAATACGAAACGATACTCGACAATGCACATTTGATCGTCTGGC    400
    GGCGACCGCAAATAATAACCAGTCCTAAGTGACGACTGGAAAGGCTGGACCATGCTTATGCTTTGCTATGAGCTGTTACGTGTAAACTAGCAGACGCCG
101  P  L  A  F  I  I  G  Q  D  S  L  L  T  F  P  T  W  Y  E  Y  E  T  I  L  D  N  A  H  L  I  V  C  R  R    134

401 GTCCAGGTTACCCACTGAAATGGCTGAACCGCAATACCAGCAGCGCAATACGCAATTCATTGACACATAACCCGGAAGATCTTCACCTTCAGCCTGCCGG    500
    CAGGTCCAATGGGTGACTTTACCGACTTGGCGTTATGGTCGTCGCGTTATGCCTGTCCGACCTTCGTTACCGACCTCTAGAAGTGGAAGTGGACGGCC
135  P  G  Y  P  L  E  M  A  Q  P  Q  Y  Q  Q  W  L  E  D  H  L  T  H  N  P  E  D  L  H  L  Q  P  A  G    167

501 TAAAATTTATCTGGCTGAAACGCCCTGTTTAACATCTCGGCGACCATCATCCGGCGAACGTTTGCAAAACGGTGAATCATGTGAGGATTTATTGCCGAA    600
    ATTTTAAATATGACCGACTTTGCGGGCACCAAATTGTAGAGCCGCTGGTAGGCCGCTGCAAACGTTTTGCCACTTAGTACACTCCTAAATAACGGCCTT
168  K  I  Y  L  A  E  T  P  W  F  N  I  S  A  T  I  I  R  E  R  L  Q  N  G  E  S  C  E  D  L  L  P  E    200

601 CCGGTACTGACTTACATTAACCAACAAGGCTTGTATCGCTGA                                                          642
    GGCCATGACTGAATGTAATTGGTTGTTCCGAACATAGCGACT
201  P  V  L  T  Y  I  N  Q  Q  G  L  Y  R  *                                                            214
```

(SEQ ID NO: 16)
(SEQ ID NO: 18)
(SEQ ID NO: 17)

FIG. 6

USE OF YACM AND YQEJ, ESSENTIAL BACTERIAL GENES AND POLYPEPTIDES AND THEIR USE

FIELD OF THE INVENTION

The invention relates to the use of yacM and yqeJ, which are essential bacterial genes, in identifying antibacterial agents.

BACKGROUND OF THE INVENTION

Bacterial infections may be cutaneous, subcutaneous, or systemic. Opportunistic bacterial infections can be life threatening, especially in patients afflicted with AIDS or other diseases that compromise the immune system. Most bacteria that are pathogenic to humans are gram-positive bacteria. The bacterium *Streptococcus pneumoniae*, for example, typically infects the respiratory tract and can cause lobar pneumonia, as well as meningitis, sinusitis, and other infections.

SUMMARY OF THE INVENTION

The invention is based on the discovery that the yacM and yqeJ genes of the gram positive bacterium *Streptococcus pneumoniae*, termed "S-yacM" and "S-yqeJ," are essential for survival. Thus, the essential polypeptides that these genes encode are useful targets for identifying compounds that are inhibitors of the bacteria in which the polypeptides are expressed. Such inhibitors can inhibit bacterial growth by inhibiting the activity of an essential protein, or by inhibiting transcription of an essential gene or translation of the mRNA transcribed from the essential gene. The amino acid and nucleic acid sequences of the Streptococcus yacM and yqeJ polypeptides and genes are set forth in FIGS. 1 and 2, as summarized in Table 1.

TABLE 1

Essential Nucleic Acids and Polypeptides

| Essential Nucleic Acid or Polypeptide | FIG NO. | SEQ ID NO. OF CODING STRAND | SEQ ID NO. OF AMINO ACID SEQUENCE | SEQ ID NO. OF NON-CODING STRAND |
|---|---|---|---|---|
| S-yacM | 1 | 1 | 2 | 3 |
| S-yqeJ | 2 | 4 | 5 | 6 |

Identification of these essential genes allows homologs of the essential genes to be found in other strains within the species, and it allows orthologs of the essential genes to be found in other organisms (e.g., Bacillus ssp. and *E. coli*). The terms "yacM" and "yqeJ" refer to the S-yacM and S-yqeJ genes and polypeptides, as well as their homologs and orthologs, collectively. While "homologs" are structurally similar genes contained within a species, "orthologs" are functionally equivalent genes from other species (within or outside of a given genus). The yacM and yqeJ genes and polypeptides can be used in methods for identifying similar genes in pathogenic and non-pathogenic microorganisms. In particular, S-yacM and S-yqeJ genes can be used to identify orthologs of yacM and yqeJ genes in other species (e.g., other gram positive bacteria, and other bacteria generally). Examples of orthologs of these Streptococcus genes are summarized in Table 2. As shown in Table 2, the Streptococcus yacM gene has an ortholog in *B. subtilis*, termed "B-yacM," and an ortholog in *E. coli*, termed "ygbP." The Streptococcus yqeJ gene also has an ortholog in *B. subtilis*, termed "B-yqeJ," and an ortholog in *E. coli*, termed "ybeN." Having identified such orthologous genes as essential, these orthologous genes and the polypeptides encoded by these orthologs can be used to identify compounds that inhibit the growth of the host organism (e.g., compounds that inhibit the activity of an essential protein, or inhibit transcription of an essential gene).

TABLE 2

Orthologs of Essential Nucleic Acids and Polypeptides

| Essential Nucleic Acid or Polypeptide | Ortholog | FIG. Number of Ortholog | SEQ ID NO. of Coding Strand of Ortholog | SEQ ID NO. of Amino Acid Sequence of Ortholog | SEQ ID NO. of Non-coding Strand of Ortholog |
|---|---|---|---|---|---|
| yacM | *B. subtilis* B-yacM Subtilist Accession No. BG10152 Swissprot Accession No. Q06755 | 3 | 7 | 8 | 9 |
| yacM | *E. coli* ygbP (new name ISPD) GenBank Accession No. g1789104 Colibri Accession No. EG13110 | 4 | 10 | 11 | 12 |
| yqeJ | *B. subtilis* B-yqeJ Subtilist Accession No. BG11638 Swissprot Accession No. P54455 | 5 | 13 | 14 | 15 |
| yqeJ | *E. coli* ybeN (new name NADD) GenBank Accession No. g1786856 Colibri Accession No. EG13241 | 6 | 16 | 17 | 18 |

The yacM and yqeJ polypeptides and genes described herein include the polypeptides and genes set forth in FIGS. 1 and 2 herein, as well as isozymes, allelic variants, and conservative variants of the sequences set forth in FIGS. 1 and 2. For example, the invention includes a gene that encodes a yacM or yqeJ polypeptide but which gene includes one or more point mutations, deletions, or promoter variants, provided that the resulting essential polypeptide retains a biological function of a yacM or yqeJ polypeptide as determined, for example, in a conventional complementation assay. Also encompassed by the terms yacM gene and yqeJ gene are degenerate variants of the nucleic acid sequences set forth in FIGS. 1–6. Degenerate variants of a nucleic acid sequence exist because of the degeneracy of the amino acid code; thus, those sequences that vary from the sequences shown in FIGS. 1–6, but which nonetheless encode a yacM or yqeJ polypeptide are degenerate variants.

Likewise, because of the similarity in the structures of amino acids, conservative variations (as described herein) can be made in the amino acid sequence of the yacM or yqeJ polypeptide while retaining the function of the polypeptide (e.g., as determined in a conventional complementation assay). Other yacM and yqeJ polypeptides and genes identified in additional bacterial strains may be such conservative variations or degenerate variants of the particular yacM or yqeJ polypeptide and nucleic acid set forth in FIGS. 1–6 (SEQ ID NOs:1–18). The yacM genes and polypeptides share at least 80%, e.g., 90% or 95%, sequence identity with the sequences shown in FIGS. 1, 3, or 4. Regardless of the percent sequence identity between the yacM sequence and the sequence shown in FIGS. 1, 3 or 4, the yacM genes and polypeptides that can be used in the methods of the invention preferably are able to complement for the lack of yacM function (e.g., in a temperature-sensitive mutant) in a standard complementation assay.

Additional yacM genes that are identified and cloned from additional bacterial strains, and pathogenic, gram positive strains in particular, can be used to produce yacM polypeptides for use in the various methods described herein, e.g., for identifying antibacterial agents. Likewise, the term "yqeJ" encompasses isozymes, variants, and conservative variations of the sequences depicted in FIGS. 2, 5, or 6.

In various embodiments, the essential polypeptide used in the assays described herein is derived from a non-pathogenic or pathogenic gram-positive bacterium. For example, the polypeptide can be derived from a Streptococcus strain, such as *Streptococcus pneumoniae, Streptococcus pyogenes, Streptococcus agalactiae, Streptococcus endocarditis, Streptococcus faecium, Streptococcus sangus, Streptococcus viridans,* and *Streptococcus hemolyticus.* Suitable orthologs of the essential genes can be derived from a wide spectrum of bacteria, such as *E. coli* and *Bacillus subtilis.*

Because the genes described herein have been shown to be essential for survival, the essential genes and polypeptides encoded by these essential genes, as well as their homologs and orthologs, can be used to identify antibacterial agents. Such antibacterial agents can readily be identified with high throughput assays to detect inhibition of the metabolic pathway in which the essential polypeptide participates. This inhibition can be caused by small molecules interacting with (e.g., binding directly or indirectly to) the essential polypeptide or other essential polypeptides in that pathway.

In an exemplary assay, but not the only assay, a promoter that responds to depletion of the essential polypeptide by upregulation or downregulation is linked to a reporter gene (e.g., β-galactosidase, gus, or GFP), as described herein. A bacterial strain containing this reporter gene construct is then exposed to test compounds. Compounds that inhibit the yacM or yqeJ polypeptide (or other polypeptides in the essential pathway in which the polypeptide participates) will cause a functional depletion of the yacM or yqeJ polypeptide and therefore lead to an upregulation or downregulation of expression of the reporter gene. Because the polypeptides described herein are essential for the survival of bacteria, compounds that inhibit the essential polypeptides in such an assay are candidate antibacterial compounds and can be further tested, if desired, in conventional susceptibility assays to determine if these compounds are antibacterial agents.

In other suitable methods, screening for antibacterial agents is accomplished by (i) identifying those compounds that interact with or bind to a yacM or yqeJ polypeptide and (ii) further testing such compounds for their ability to inhibit bacterial growth in vitro or in vivo.

The invention also provides methods of preparing an antibacterial agent. The methods include: screening multiple test compounds by the methods described herein; identifying candidate antibacterial compounds that interact with yacM or yqeJ; isolating one or more lead compounds from the candidate compounds; identifying a lead compound that inhibits bacterial growth; selecting a lead compound that inhibits bacterial growth; and formulating the selected lead compound as an antibacterial agent. A "lead compound" is a test compound that binds to yacM or yqeJ with a statistically significant binding affinity. For example, the binding can be sufficient to inhibit an essential function of the protein.

If desired, lead compounds can subsequently be derivatized using conventional medicinal chemistry methods, as described herein. Thus, the invention includes methods for preparing an antibacterial agent by: screening multiple test compounds by the methods described herein; identifying candidate compounds that interact with yacM or yqeJ; isolating one or more lead compounds from the candidate compounds; derivatizing the lead compound(s), thereby producing a derivative of the lead compound; identifying derivatives that inhibit bacterial growth; and formulating the derivative as an antibacterial agent (e.g., by admixture with a pharmaceutically acceptable carrier). Antibacterial agents prepared by such methods also are included within the invention and can be used in methods for treating a bacterial infection in an organism.

Typically, the test compound will be a small organic molecule. Alternatively, the test compound can be a test polypeptide (e.g., a polypeptide having a random or predetermined amino acid sequence; or a naturally-occurring or synthetic polypeptide) or a nucleic acid, such as a DNA or RNA molecule. The test compound can be a naturally-occurring compound or it can be synthetically produced, if desired. Synthetic libraries, chemical libraries, bodily fluids (e.g., urine, sweat, tears, blood, or CSF) and the like can be screened to identify compounds that bind to the yacM or yqeJ polypeptide. More generally, binding of a test compound to the polypeptide can be detected either in vitro or in vivo. If desired, the above-described methods for identifying compounds that modulate the expression of the polypeptides of the invention can be combined with measuring the levels of the yacM or yqeJ polypeptide expressed in the cells, e.g., by performing a Western blot analysis using antibodies that bind to a yacM or yqeJ polypeptide.

Regardless of the source of the test compound, the yacM and yqeJ polypeptides described herein can be used to identify compounds that inhibit (i) the activity of a yacM or yqeJ protein, (ii) transcription of a yacM or yqeJ gene, or (iii) translation of the mRNA transcribed from the yacM or yqeJ gene. These antibacterial agents can be used to inhibit a wide spectrum of pathogenic or non-pathogenic bacterial strains.

In other embodiments, the invention includes pharmaceutical formulations that include a pharmaceutically acceptable excipient and an antibacterial agent identified using the methods described herein. In particular, the invention includes pharmaceutical formulations that contain antibacterial agents that inhibit the growth of, or kill, pathogenic bacterial strains (e.g., pathogenic gram positive bacterial strains such as pathogenic Streptococcus strains). Such pharmaceutical formulations can be used in a method of treating a bacterial infection in an organism (e.g., a Streptococcus infection). Such a method entails administering to the organism a therapeutically effective amount of the pharmaceutical formulation, i.e., an amount sufficient to ameliorate signs and/or symptoms of the bacterial infection. In particular, such pharmaceutical formulations can be used to treat bacterial infections in mammals such as humans and domesticated mammals (e.g., cows, pigs, horses, dogs, and cats), and in plants. The efficacy of such antibacterial agents in humans can be reasonably predicted by using animal model systems well known to those of skill in the art (e.g., mouse and rabbit model systems of, for example, streptococcal pneumonia).

Purified or isolated antibodies that specifically bind to a yacM or yqeJ polypeptide can be used in the methods of the invention. An antibody "specifically binds" to a particular antigen, e.g., a yacM or yqeJ polypeptide, when it binds to that antigen, but does not substantially recognize and bind to other molecules in a sample, e.g., a biological sample, that naturally includes a yacM or yqeJ polypeptide.

The invention offers several advantages. For example, the methods for identifying antibacterial agents can be configured for high throughput screening of numerous candidate antibacterial agents. Because the yacM and yqeJ genes disclosed herein are thought to be highly conserved, antibacterial drugs targeted to these genes or their gene products are expected to have a broad spectrum of antibacterial activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWINGS

FIG. 1 is a listing of the coding strand, amino acid, and non-coding strand sequences of the S-yacM polypeptide and gene from a *Streptococcus pneumoniae* strain (SEQ ID NOs:1, 2, and 3, respectively).

FIG. 2 is a representation of the coding strand, amino acid, and non-coding strand sequences of the S-yqeJ polypeptide and gene from a *Streptococcus pneumoniae* strain (SEQ ID NOs:4, 5, and 6, respectively).

FIG. 3 is a representation of the coding strand, amino acid, and non-coding strand sequences of the B-yacM polypeptide and gene from a *B. subtilis* strain (SEQ ID NOs:7, 8, and 9, respectively).

FIG. 4 is a representation of the coding strand, amino acid, and non-coding strand sequences of the ygbP polypeptide and gene from an *E. coli* strain (SEQ ID NOs:10, 11, and 12, respectively).

FIG. 5 is a representation of the coding strand, amino acid, and non-coding strand sequences of the B-yqeJ polypeptide and gene from a *B. subtilis* strain (SEQ ID NOs:13, 14, and 15, respectively).

FIG. 6 is a representation of the coding strand, amino acid, and non-coding strand sequences of the ybeN polypeptide and gene from an *E. coli* strain (SEQ ID NOs:16, 17, and 18, respectively).

DETAILED DESCRIPTION

Figure 7:
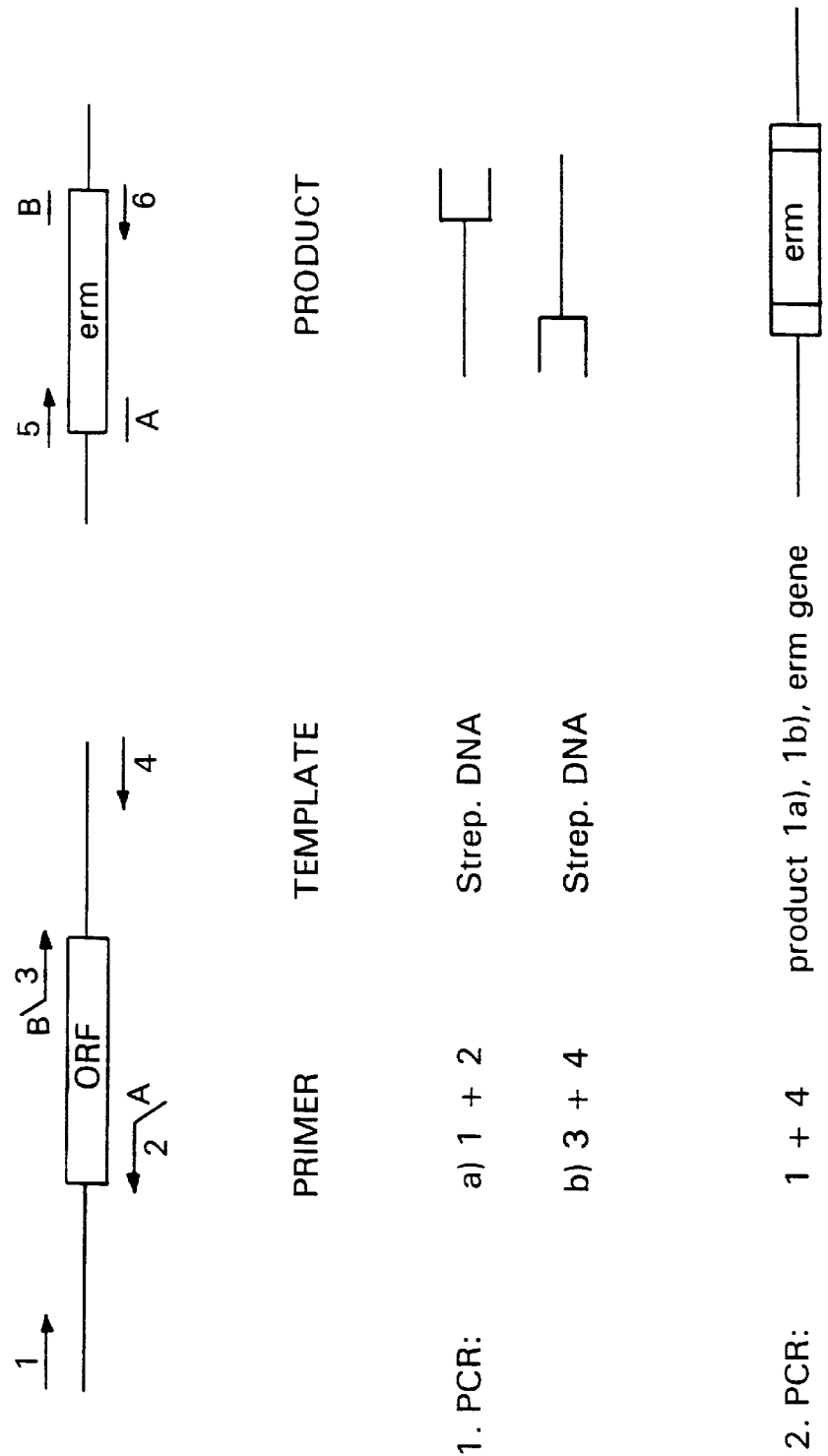
FIG. 7 is a schematic representation of the PCR strategy used to produce DNA molecules used for targeted deletions of the yacM and yqeJ genes in *Streptococcus pneumoniae*.

At least two genes in the bacterium *Streptococcus pneumoniae* have been found to be essential for the survival of these bacteria. These so-called essential genes, yacM and yqeJ, encode what are referred to herein as essential polypeptides. The yacM and yqeJ genes are useful molecular tools for identifying similar genes in pathogenic and non-pathogenic bacteria. The essential polypeptides are useful targets for identifying compounds that are inhibitors of the pathogens in which the essential polypeptides are expressed.

Nucleic Acids and Polypeptides

Nucleic acids that can be used in the methods of the invention include both RNA and DNA, including genomic DNA and synthetic (e.g., chemically synthesized) DNA. Nucleic acids can be double-stranded or single-stranded. If single-stranded, the nucleic acid may be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An isolated nucleic acid is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an isolated nucleic acid fragment is a nucleic acid fragment that is not naturally occurring as a fragment and would not be found in the natural state.

A nucleic acid sequence that is substantially identical to a yacM or yqeJ nucleotide sequence is at least 80% (e.g., at least 85%, 90%, or 95%) identical to the nucleotide sequence of yacM or yqeJ as represented by the sequences depicted in FIGS. 1–6. For purposes of comparison of nucleic acids, the length of the reference nucleic acid sequence will generally be at least 40 nucleotides, e.g., at least 60 nucleotides or more nucleotides.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of overlapping positions×100). Preferably, the two sequences are the same length.

The determination of percent identity or homology between two sequences can be accomplished using a mathematical algorithm. A suitable, mathematical algorithm utilized for the comparison of two sequences is the algorithm of Karlin and Altschul (1990) Proc. Nat'l. Acad. Sci. USA 87:2264–2268, modified as in Karlin and Altschul (1993) Proc. Nat'l. Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences homologous to the yacM or yqeJ nucleic acid molecules of the invention. BLAST protein searches can be performed with the XBLAST program, score=50, wordlength=3 to obtain amino acid sequences homologous to the yacM or yqeJ protein molecules of the invention. To obtain gapped alignments for comparison purposes, Gapped BLAST can be utilized as described in Altschul et al., (1997) Nucleic Acids Res. 25:3389–3402. When utilizing BLAST and Gapped BLAST programs, the default parameters of the respective programs (e.g., XBLAST and NBLAST) can be used. See, e.g., http://www.ncbi.nlm.nih.gov.

The yacM and yqeJ polypeptides useful in practicing the invention include, but are not limited to, recombinant polypeptides and natural polypeptides. Also useful in the invention are nucleic acid sequences that encode forms of the yacM and yqeJ polypeptides in which naturally occurring amino acid sequences are altered or deleted. Preferred nucleic acids encode polypeptides that are soluble under normal physiological conditions. Also within the invention are nucleic acids encoding fusion proteins in which a portion of the yacM or yqeJ polypeptide is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes, for example, isolated polypeptides (and the nucleic acids that encode these polypeptides) that include a first portion and a second portion; the first portion includes, e.g., a yacM or yqeJ polypeptide, and the second portion includes an immunoglobulin constant (Fc) region or a detectable marker.

The fusion partner can be, for example, a polypeptide that facilitates secretion, e.g., a secretory sequence. Such a fused polypeptide is typically referred to as a preprotein. The secretory sequence can be cleaved by the host cell to form the mature protein. Also within the invention are nucleic acids that encode a yacM or yqeJ polypeptide fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequences represented by SEQ ID NO:1, 3, 4, 6, 7, 9, 10, 12, 13, 15, 16, or 18 or their complements. The hybridizing portion of the hybridizing nucleic acids is typically at least 15 (e.g., 20, 25, 30, or 50) nucleotides in length. The hybridizing portion of the hybridizing nucleic acid is at least 80%, e.g., at least 95%, or at least 98%, identical to the sequence of a portion or all of a nucleic acid encoding a yacM or yqeJ polypeptide, or its complement. Hybridizing nucleic acids of the type described herein can be used as a cloning probe, a primer (e.g., a PCR primer), or a diagnostic probe. Nucleic acids that hybridize to the coding strands shown herein are considered "antisense oligonucleotides."

Also useful in the invention are various engineered cells, e.g., transformed host cells, that contain a yacM or yqeJ nucleic acid described herein. A transformed cell is a cell into which (or into an ancestor of which) has been introduced, by means of recombinant DNA techniques, a nucleic acid encoding a yacM or yqeJ polypeptide. Both prokaryotic and eukaryotic cells are included, e.g., bacteria, such as Streptococcus, Bacillus, and the like.

Also useful in practicing the invention are genetic constructs (e.g., vectors and plasmids) that include a nucleic acid disclosed herein that is operably linked to a transcription and/or translation sequence to enable expression, e.g., expression vectors. A selected nucleic acid, e.g., a DNA molecule encoding a yacM or yqeJ polypeptide, is "operably linked" to a transcription and/or translation sequence when it is positioned within a nucleic acid molecule such that one or more sequence elements, e.g., a promoter, which direct transcription and/or translation of other nucleic acids, within the nucleic acid molecule can control transcription and/or translation of the selected nucleic acid.

Polypeptides encoded by the yacM and yqeJ genes also are useful in practicing the methods of the invention. The terms "protein" and "polypeptide" both refer to any chain of amino acids, regardless of length or post-translational modification (e.g., glycosylation or phosphorylation). Thus, the terms yacM polypeptide and yqeJ polypeptide include full-length, naturally occurring, isolated yacM and yqeJ proteins, respectively, as well as recombinantly or synthetically produced polypeptides that correspond to the full-length, naturally occurring proteins, or to a portion of the naturally occurring or synthetic polypeptide, provided that the portion is able to complement for yacM or yqeJ in a standard complementation assay.

A purified or isolated compound is a composition that is at least 60% by weight the compound of interest, e.g., a yacM or yqeJ polypeptide. Preferably, the preparation is at least 75% (e.g., at least 90%, 95%, or even 99%) by weight the compound of interest. Purity can be measured by any appropriate standard method, e.g., column chromatography, polyacrylamide gel electrophoresis, or HPLC analysis.

YacM and yqeJ polypeptides include an amino acid sequence substantially identical to all or a portion of a naturally occurring yacM or yqeJ polypeptide, e.g., including all or a portion of the sequences shown in FIGS. 1–6. Polypeptides "substantially identical" to the yacM or yqeJ polypeptide sequences described herein have an amino acid sequence that is at least 80% identical to the amino acid sequence of the polypeptides disclosed herein (measured as described herein). The new polypeptides can also have a greater percentage identity, e.g., 85%, 90%, 95%, or even higher. For purposes of comparison, the length of the referenced yacM or yqeJ polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a yacM or yqeJ polypeptide is preferably replaced with another amino acid residue from the same side chain family.

Alternatively, mutations can be introduced randomly along all or part of a yacM or yqeJ coding sequence, such as by saturation mutagenesis, and the resultant mutants can be screened for yacM or yqeJ polypeptide biological activity to identify mutants that retain activity. Following mutagenesis, the encoded yacM or yqeJ polypeptide can be expressed recombinantly and the activity of the protein can be determined.

Where a particular polypeptide has a specific percent identity relative to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. Alternatively, it can be a 100 amino acid long polypeptide that is 50% identical to the reference polypeptide over its entire length. Of course, other polypeptides also will meet the same criteria.

Identifying Essential Streptococcus Genes

As shown by the experiments described below, both the yacM and yqeJ genes are essential for survival of *Streptococcus pneumoniae*. *Streptococcus pneumoniae* is available from the ATCC. In general, and for the examples set forth below, essential genes can be identified by creating targeted deletions of genes of interest in bacteria, e.g., *S. pneumoniae*. These genes of interest were selected as follows. Using standard molecular biology techniques, a library containing fragments of the *Streptococcus pneumoniae* genome was made, using M13 phage or plasmid DNA as the vector. Open reading frames (ORFs) contained within this library were randomly sequenced, using primers that hybridized to the vector. The genes of interest selected for targeted deletion satisfied four criteria, as determined by comparing the sequences with the GenBank database of nucleotide sequences: (i) the ORF had no known function; (ii) the ORF had an ortholog in *Bacillus subtilis*; (iii) the ORF was conserved in other bacteria, with $p<10^{-10}$; and (iv) the ORF had no eukaryotic ortholog, with $p>10^{-3}$. The Streptococcus genes yacM and yqeJ met each of these criteria, suggesting that a compound that inhibited the yacM or yqeJ genes or gene products would have a broad spectrum of antibacterial activity.

The yacM and yqeJ genes each were replaced with a nucleic acid sequence conferring resistance to the antibiotic erythromycin (an "erm" gene). Other genetic markers can be used in lieu of this particular antibiotic resistance marker. Polymerase chain reaction (PCR) amplification was used to make a targeted deletion in the Streptococcus genomic DNA, as shown in FIG. 7. Several PCR reactions were used to produce the DNA molecules needed to carry out target deletion of the genes of interest. First, using primers 5 and 6, an erm gene was amplified from pIL252 from *B. subtilis* (available from the Bacillus Genetic Stock Center, Columbus, Ohio). Primer 5 consists of 21 nucleotides that are identical to the promoter region of the erm gene and complementary to Sequence A. Primer 5 has the sequence 5'GTG TTC GTG CTG ACT TGC ACC3' (SEQ ID NO:19). Primer 6 consists of 21 nucleotides that are complementary to the 3' end of the erm gene. Primer 6 has the sequence 5'GAA TTA TTT CCT CCC GTT AAA3' (SEQ ID NO:20). PCR amplification of the erm gene was carried out under the following conditions: 30 cycles of 94° C. for 1 minute, 55° C for 1 minute, and 72° C. for 1.5 minutes, followed by one cycle of 72° C. for 10 minutes.

In the second and third PCR reactions, sequences flanking the gene of interest were amplified and produced as hybrid DNA molecules that also contained a portion of the erm gene. The second reaction produced a double-stranded DNA molecule (termed "Left Flanking Molecule") that includes sequences upstream of the 5' end of the gene of interest and the first 21 nucleotides of the erm gene. As shown in FIG. 7, this reaction utilized primer 1, which is 21 nucleotides in length and identical to a sequence that is located approximately 500 bp upstream of the translation start site of the gene of interest. Primers 1 and 2 are gene-specific and have the sequences: 5'ACA AGT GAT TGT ACC AAC TGC 3' (SEQ ID NO:21); and 5'GGT GCA AGT CAG CAC GAA CAC AAT AGT TCG ATT GTC ATA GGC 3' (SEQ ID NO:22), respectively, for yqeJ.

For yacM, primers 1 and 2 have the sequences: 5'GCA AAG GGC AAG AAA AAT GA 3' (SEQ ID NO:23), and 5'GGT GCA AGT CAG CAC GAA CAC TTG GCA AGT TAC TGA TCC CC 3' (SEQ ID NO:24), respectively. Primer 2 for yacM is 41 nucleotides in length, with 21 of the nucleotides at the 3' end of the primer being complementary to the 5' end of the sense strand of the gene of interest. The 21 nucleotides at the 5' end of the primer were identical to Sequence A and are therefore complementary to the 5' end of the erm gene. Thus, PCR amplification using primers 1 and 2 produced the left flanking DNA molecule, which is a hybrid DNA molecule containing a sequence located upstream of the gene of interest and 21 base pairs of the erm gene, as shown in FIG. 7.

The third PCR reaction was similar to the second reaction, but produced the right flanking DNA molecule, shown in FIG. 7. The right flanking DNA molecule contains 21 base pairs of the 3' end of the erm gene, a 21 base pair portion of the 3' end of the gene of interest, and sequences downstream of the gene of interest. This right flanking DNA molecule was produced with gene-specific primers 3 and 4. For yqeJ, primers 3 and 4 have the sequences 5'TTT AAC GGG AGG AAA TAA TTC TGC TAG ACT ACA TCG AGA AGG 3' (SEQ ID NO:25), and 5'GAT ACT CCA CGG TAC GAG CTG 3' (SEQ ID NO:26), respectively. For yacM, primers 3 and 4 have the sequences 5'TTT AAC GGG AGG AAA TAA TTC AGG AAA AGA TGT GGG TTT GG 3' (SEQ ID NO:27), and 5'CTT CCA TCT CCA ATA ACG GC 3' (SEQ ID NO:28), respectively. Primer 3 for yacM is 41 nucleotides; the 21 nucleotides at the 5' end of Primer 3 are identical to Sequence B and therefore are identical to the 3' end of the erm gene. The 21 nucleotides at the 3' end of Primer 3 are identical to the 3' end of the gene of interest.

Primer 4 for yacM is 20 nucleotides in length and is complementary to a sequence located approximately 500 bp downstream of the gene of interest.

PCR amplification of the left and right flanking DNA molecules was carried out, separately, in 50 µl reaction mixtures containing: 1 µl Streptococcus pneumoniae (RX1) DNA (0.25 µg), 2.5 µl Primer 1 or Primer 4 (10 pmol/µl), 2.5 µl Primer 2 or Primer 3 (20 pmol/µl), 1.2 µl a mixture dNTPs (10 mM each), 37 µl H$_2$O, 0.7 µl Taq polymerase (5U/µl), and 5 µl 10× Taq polymerase buffer (10 mM Tris, 50 mM KCl, 2.5 mM MgCl$_2$). The left and right flanking DNA molecules were amplified using the following PCR cycling program: 95° C. for 2 minutes; 72° C. for 1 minute; 94° C. for 30 seconds; 49° C. seconds; 72° C. for 1 minute; repeating the 94° C., 49° C., and 72° C. incubations 30 times; 72° C. for 10 minutes and then stopping the reactions. A 15 µl aliquot of each reaction mixture then was electrophoresed through a 1.2% low melting point agarose gel in TAE buffer and then stained with ethidium bromide. Fragments containing the amplified left and right flanking DNA molecules were excised from the gel and purified using the QIAQUICK™ gel extraction kit (Qiagen, Inc.) Other art-known methods for amplifying and isolating DNA can be substituted. The flanking left and right DNA fragments were eluted into 30 µl TE buffer at pH 8.0.

The amplified erm gene and left and right flanking DNA molecules were then fused together to produce the fusion product, as shown in FIG. 7. The fusion PCR reaction was carried out in a volume of 50 µl containing: 2 µl of each of the left and right flanking DNA molecules and the erm gene PCR product; 5 µl of 10× buffer; 2.5 µl of Primer 1 (10 pmol/µl); 2.5 µl of Primer 4 (10 pmol/µl), 1.2 µl dNTP mix (10 mM each) 32 µl H$_2$O, and 0.7 µl Taq polymerase. The PCR reaction was carried out using the following cycling program: 95° C. for 2 minutes; 72° C. for 1 minute; 94° C. for 30 seconds, 48° C. for 30 seconds; 72° C. for 3 minutes; repeat the 94° C., 48° C. and 72° C. incubations 25 times; 72° C. for 10 minutes. After the reaction was stopped, a 12 µl aliquot of the reaction mixture was electrophoresed through an agarose gel to confirm the presence of a final product of approximately 2 kb.

Figure 8:
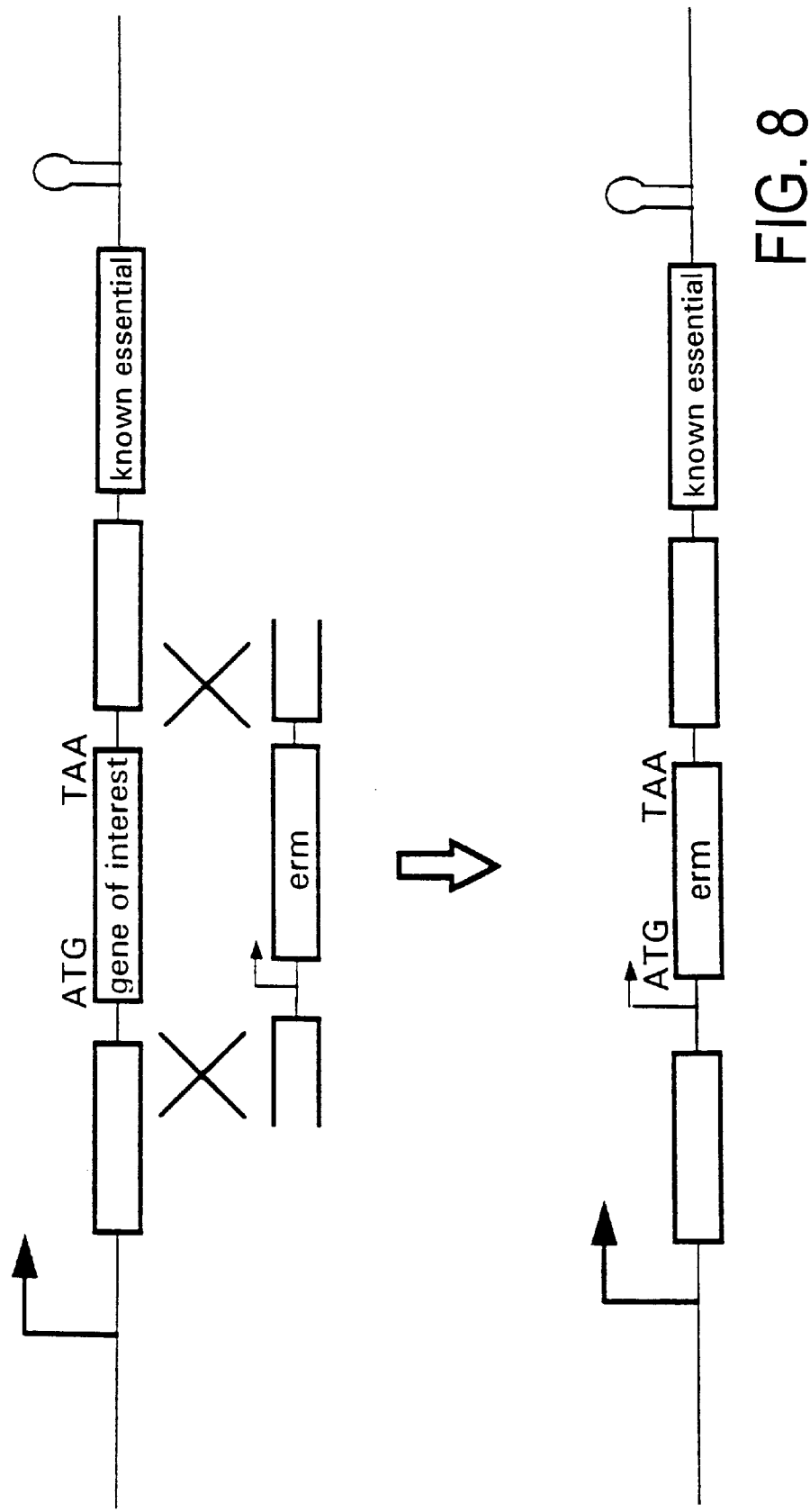
FIG. 8 is a schematic representation of the strategy used to produce targeted deletions of the yacM and yqeJ genes in *Streptococcus pneumoniae*.

A 5 µl aliquot of the fusion product was used to transform S. pneumoniae grown on a medium containing erythromycin in accordance with standard techniques. As shown in FIG. 8, the fusion product and the S. pneumoniae genome undergo a homologous recombination event so that the erm gene replaces the chromosomal copy of the gene of interest, thereby creating a gene knockout. Disruption of an essential gene results in no growth on a medium containing erythromycin. Using this gene knockout method, the yacM and yqeJ genes were identified as being essential for survival.

Identification of Orthologs of Essential Genes

Having shown that the yacM and yqeJ genes are essential for survival of Streptococcus, it can be expected that orthologs or homologs of these genes, when present in other organisms, for example B. subtilis or E. coli, are essential for survival of those organisms as well. The coding sequences of yacM and yqeJ were used to search the GenBank database of nucleotide sequences, and orthologs of each sequence were identified in B. subtilis and E. coli. Sequence comparisons were performed using the Basic Local Alignment Search Tool (BLAST) (Altschul et al., J. Mol. Biol., 215:403–410, 1990). The percent sequence identity shared by the essential polypeptides and their orthologs was determined using the GAP program from the Genetics Computer Group (GCG) Wisconsin Sequence Analysis Package (Wisconsin Package Version 9.1; Madison, Wis.). The default parameters for gap weight (12) and length weight (4) were used.

Typically, essential polypeptides and their homologs or orthologs share at least 25% (e.g., at least 30% or 40%) sequence identity. Typically, the DNA sequences encoding essential polypeptides and their homologs or orthologs share at least 20% (e.g., at least 30%, 35%, 40% or 45%) sequence identity. Bioinformatics analysis of the yacM and yqeJ genes showed that these genes are widely conserved among bacteria. To confirm that the identified orthologs of yacM and yqeJ are essential for survival of other bacteria, each of the orthologous genes was, separately, deleted from the genome of the host organism. Such deletion strains have been constructed and do not survive, confirming the essential nature of the polypeptides. The fact that the B. subtilis and E. coli orthologs of the yacM and yqeJ genes also are essential for survival suggests that these genes are essential in all bacteria where they are present. Therefore, an antibacterial drug targeted to these genes or their gene products is expected to have a broad spectrum of antibacterial activity.

Identification of Essential Genes and Polypeptides in Additional Bacterial Strains Having identified the yacM and yqeJ genes and their B. subtilis and E. coli orthologs as essential for survival, these genes, or fragments thereof, can be used to detect homologous or orthologous genes that are essential in yet other organisms. In particular, these genes can be used to analyze various pathogenic and non-pathogenic strains of bacteria. Fragments of a nucleic acid (DNA or RNA) encoding an essential polypeptide, homolog or ortholog (or sequences complementary thereto) can be used as probes in conventional nucleic acid hybridization assays of pathogenic bacteria. For example, nucleic acid probes (which typically are 8–30, or usually 15–20, nucleotides in length) can be used to detect yacM and yqeJ genes in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragments thereof, is labeled and used to screen a genomic library constructed from mRNA obtained from a bacterial strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under moderate to stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having>95% identity with the probe are sought, the final wash temperature is decreased by 5° C.). In practice, the change in $T_m$ can be between 0.5° C. and 1.5° C. per 1% mismatch.

Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic bacterial strains can be screened. For example, such strains can be screened for expression of essential genes by Northern blot analysis. Upon detection of transcripts of the yacM or yqeJ genes, libraries can be constructed from RNA isolated from the appropriate strain, utilizing standard techniques well known to those of skill in the art. Alternatively, a total genomic DNA library can be screened using a yacM or yqeJ gene probe (or a probe directed to a homolog thereof).

New gene sequences can be isolated, for example, by performing PCR using two degenerate oligonucleotide primer pools designed on the basis of nucleotide sequences within the yacM or yqeJ genes disclosed herein. The template for the reaction can be DNA obtained from strains known or suspected to express an allele of yacM or yqeJ ortholog thereof. The PCR product can be subcloned and sequenced to ensure that the amplified sequences represent the sequences of a new essential nucleic acid sequence.

Synthesis of the various yacM and yqeJ polypeptides (or an antigenic fragment thereof) for use as antigens, or for other purposes, can readily be accomplished using any of the various art-known techniques. For example, the polypeptide, or an antigenic fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or in insect cells (e.g., by using a baculovirus-based expression vector).

Proteins and polypeptides can also be produced in plant cells, if desired. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Manassas, Va.; also, see, e.g., Ausubel et al., Current Protocols in Molecular Biology, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in Cloning Vectors: A Laboratory Manual (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, the yacM and yqeJ polypeptides can be produced as fusion proteins. For example, the expression vector pUR278 (Ruther et al., EMBO J., 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary expression system, a baculovirus such as *Autographa californica* nuclear polyhedrosis virus (AcNPV), which grows in *Spodoptera frugiperda* cells, can be used as a vector to express foreign genes. A coding sequence encoding a yacM or yqeJ polypeptide can be cloned into a non-essential region (for example the polyhedrin gene) of the viral genome and placed under control of a promoter, e.g., the polyhedrin promoter or an exogenous promoter. Successful insertion of a gene encoding a yacM or yqeJ polypeptide can result in inactivation of the polyhedrin gene and production of non-occluded recombinant virus (i.e., virus lacking the proteinaceous coat encoded by the polyhedrin gene). These recombinant viruses are then typically used to infect insect cells (e.g., *Spodoptera frugiperda* cells) in which the inserted gene is expressed (see, e.g., Smith et al., J. Virol., 46:584, 1983; Smith, U.S. Pat. No. 4,215,051). If desired, mammalian cells can be used in lieu of insect cells, provided that the virus is engineered such that the gene encoding the desired polypeptide is placed under the control of a promoter that is active in mammalian cells.

In mammalian host cells, a number of viral-based expression systems can be utilized. When an adenovirus is used as an expression vector, the nucleic acid sequence encoding the essential polypeptide or homolog can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing an essential gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., Methods in Enzymol., 153:516, 1987).

The yacM and yqeJ polypeptides can be expressed individually or as fusions with a heterologous polypeptide, such as a signal sequence or other polypeptide having a specific cleavage site at the N- and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the yacM or yqeJ polypeptide can be produced by a stably-transfected mammalian cell line. A number of vectors suitable for stable transfection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the plasmid and, therefore, the essential polypeptide-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyl-transferase genes, and adenine phosphoribosyltransferase genes, which can be employed in tk, hgprt, or aprt cells, respectively. In addition, gpt, which confers resistance to mycophenolic acid (Mulligan et al., Proc. Natl. Acad. Sci. USA, 78:2072, 1981); neo, which confers resistance to the aminoglycoside G-418 (Colberre-Garapin et al., J. Mol. Biol., 150:1, 1981); and hygro, which confers resistance to hygromycin (Santerre et al., Gene, 30:147, 1981), can be used.

Alternatively, any fusion protein can be readily purified by utilizing an antibody or other molecule that specifically binds the fusion protein being expressed. For example, a system described in Janknecht et al., Proc. Natl. Acad. Sci. USA, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, yacM or yqeJ, or a portion thereof, can be fused to an immunoglobulin Fc domain. Such a fusion protein can be readily purified using a protein A column, for example. Moreover, such fusion proteins permit the production of a chimeric form of a yacM or yqeJ polypeptide having increased stability in vivo.

Once the recombinant yacM or yqeJ polypeptide is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-yacM antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate an essential polypeptide (e.g., a yacM-maltose binding fusion protein, a yacM-$\beta$-galactosidase fusion protein, or a yacM-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, Laboratory Techniques In Biochemistry and Molecular Biology, eds., Work and Burdon, Elsevier, 1980).

Given the amino acid sequences described herein, polypeptides useful in practicing the invention, particularly fragments of yacM and yqeJ polypeptides, can be produced by standard chemical synthesis (e.g., by the methods described in Solid Phase Peptide Synthesis, 2nd ed., The Pierce Chemical Co., Rockford, Ill., 1984) and used as antigens, for example.

Antibodies

The yacM and yqeJ polypeptides (or antigenic fragments or analogs of such polypeptides) can be used to raise antibodies useful in the invention, and such polypeptides can be produced by recombinant or peptide synthetic techniques (see, e.g., Solid Phase Peptide Synthesis, supra; Ausubel et al., supra). Likewise, antibodies can be raised against homologs or orthologs of yacM and yqeJ (or antigenic fragments and analogs of such homologs and orthologs). In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (Bacille Calmette-Guerin) and *Corynebacterium parvum*. Polyclonal antibodies are heterogeneous populations of antibody molecules derived from the sera of the immunized animals.

Antibodies useful in the invention include monoclonal antibodies, polyclonal antibodies, humanized or chimeric antibodies, single chain antibodies, Fab fragments, F(ab')2 fragments, and molecules produced using a Fab expression library.

Monoclonal antibodies (mAbs), which are homogeneous populations of antibodies to a particular antigen, can be prepared using a yacM or yqeJ polypeptide or fragment thereof and standard hybridoma technology (see, e.g., Kohler et al., Nature, 256:495, 1975; Kohler et al., Eur. J. Immunol., 6:511, 1976; Kohler et al., Eur. J. Immunol., 6:292, 1976; Hammerling et al., in Monoclonal Antibodies and T Cell Hybridomas, Elsevier, N.Y., 1981; Ausubel et al., supra).

In particular, monoclonal antibodies can be obtained by any technique that provides for the production of antibody molecules by continuous cell lines in culture, such as those described in Kohler et al., Nature, 256:495, 1975, and U.S. Pat. No. 4,376,110; the human B-cell hybridoma technique (Kosbor et al., Immunology Today, 4:72, 1983; Cole et al., Proc. Natl. Acad. Sci. USA, 80:2026, 1983); and the EBV-hybridoma technique (Cole et al., Monoclonal Antibodies and Cancer Therapy, Alan R. Liss, Inc., pp. 77–96, 1983). Such antibodies can be of any immunoglobulin class including IgG, IgM, IgE, IgA, IgD, and any subclass thereof. The hybridomas producing the mAbs can be cultivated in vitro or in vivo.

Once produced, polyclonal or monoclonal antibodies are tested for specific recognition of yacM or yqeJ in an immunoassay, such as a Western blot or immunoprecipitation analysis using standard techniques, e.g., as described in Ausubel et al., supra. Antibodies that specifically bind to a yacM or yqeJ polypeptide, are useful in the invention. For example, such antibodies can be used in an immunoassay to detect an essential polypeptide in pathogenic or non-pathogenic strains of bacteria.

Preferably, antibodies are produced using fragments of the yacM or yqeJ polypeptides that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in E. coli and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant essential polypeptide or homolog, or unrelated control proteins, such as glucocorticoid receptor, chloramphenicol acetyltransferase, or luciferase.

Techniques developed for the production of "chimeric antibodies" (Morrison et al., Proc. Natl. Acad. Sci., 81:6851, 1984; Neuberger et al., Nature, 312:604, 1984; Takeda et al., Nature, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778; 4,946,778; and 4,704,692) can be adapted to produce single chain antibodies against an essential polypeptide or homolog or ortholog thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to F(ab')2 fragments, which can be produced by pepsin digestion of the antibody molecule, and Fab fragments, which can be generated by reducing the disulfide bridges of F(ab')2 fragments. Alternatively, Fab expression libraries can be constructed (Huse et al., Science, 246:1275, 1989) to allow rapid and easy identification of monoclonal Fab fragments with the desired specificity.

Polyclonal and monoclonal antibodies that specifically bind to a yacM or yqeJ polypeptide, can be used, for example, to detect expression of a yacM or yqeJ gene, in another bacteria. For example, a yacM or yqeJ polypeptide can be readily detected in conventional immunoassays of bacteria cells or extracts. Examples of suitable assays include, without limitation, Western blotting, ELISAs, radioimmune assays, and the like.

Assays for Antibacterial Agents

The invention provides methods for identifying candidate antibacterial compounds and antibacterial agents. Without being bound by any particular theory as to the biological mechanism involved, the new antibacterial agents are thought to inhibit specifically (1) the function of the yacM or yqeJ polypeptide(s), or (2) expression of the yacM or yqeJ genes. In preferred methods, screening for antibacterial agents is accomplished by identifying those compounds (e.g., small organic molecules) that inhibit the activity of a yacM or yqeJ polypeptide or the expression of a yacM or yqeJ gene.

In an exemplary assay for antibacterial agents, but not the only assay, a promoter that responds to depletion of the essential polypeptide by upregulation or downregulation is operably linked to a reporter gene. To identify a promoter that is upregulated or downregulated by the depletion of yacM or yqeJ protein, the gene encoding the protein is deleted from the genome and replaced with a version of the gene in which the sequence encoding the yacM or yqeJ protein is operably linked to a regulatable promoter. The cells containing this regulatable genetic construct are kept alive by the yacM or yqeJ polypeptide produced from the genetic construct containing the regulatable promoter. However, the regulatable promoter allows the expression of the yacM or yqeJ polypeptide to be reduced to a level that causes growth inhibition. Total RNA prepared from bacteria under such growth-limiting conditions is compared with RNA from wild-type cells. Standard methods of transcriptional profiling can be used to identify mRNA species that are either more or less abundant (i.e., upregulated or downregulated) when expressed under the limiting conditions. Genomic sequence information, e.g., from GenBank, can be used to identify the promoter that drives expression of the identified RNA species. Such promoters are upregulated or downregulated by depletion of the essential polypeptide.

Having identified a promoter(s) that is upregulated or downregulated by depletion of the essential polypeptide, the promoter(s) is operably linked to a reporter gene (e.g., β-galactosidase, gus, or green fluorescent protein (GFP)). A bacterial strain containing this reporter gene construct is then exposed to test compounds. Compounds that inhibit the essential polypeptide (or other polypeptides in the essential pathway in which the essential polypeptide participates) will cause a functional depletion of the essential polypeptide and therefore lead to an upregulation or downregulation of expression of the reporter gene. Because the yacM and yqeJ polypeptides described herein are essential for the survival of bacteria, compounds that inhibit the essential polypeptides in such an assay are candidate antibacterial compounds and can be further tested, if desired, in standard susceptibility assays.

Another suitable method for identifying antibacterial compounds involves screening for small molecules that specifically interact with (i.e., bind directly or indirectly to) the yacM and yqeJ polypeptide. A variety of suitable interaction and binding assays are known in the art as described, for example, in U.S. Pat. Nos. 5,585,277 and 5,679,582, incorporated herein by reference. For example, in various conventional assays, test compounds can be assayed for their ability to interact with a yacM or yqeJ polypeptide by measuring the ability of the small molecule to stabilize the polypeptide in its folded, rather than unfolded, state. More specifically, one can measure the degree of protection from unfolding that is afforded by the test compound. Test compounds that bind to the yacM or yqeJ polypeptide with high affinity cause, for example, a large shift in the temperature at which the polypeptide is denatured. Test compounds that stabilize the essential polypeptide in a folded state can be further tested for antibacterial activity in a standard susceptibility assay.

In a related method for identifying antibacterial compounds and agents, the yacM and yqeJ polypeptides are used to isolate peptide or nucleic acid ligands that specifically bind to the polypeptides. These peptide or nucleic acid ligands are then used in a displacement screen to identify small molecules that interact with the yacM or yqeJ polypeptide. Such assays can be carried out essentially as described above.

Another suitable method for identifying inhibitors of the yacM or yqeJ polypeptides involves identifying a biochemical activity of the polypeptide and then screening for inhibitors (e.g., small molecules) of the activity using, for example, a high throughput screening method.

The polypeptides encoded by the yacM and yqeJ genes also can be used, separately or together, in assays to identify test compounds that interact with these polypeptides. Test compounds that interact with these polypeptides then can readily be tested, in conventional assays, for their ability to inhibit bacterial growth. Test compounds that interact with the yacM and yqeJ polypeptides are candidate antibacterial compounds, in contrast to compounds that do not interact with the yacM and yqeJ polypeptides. As described herein, any of a variety of art-known methods can be used to assay for the interaction of test compounds with the yacM or yqeJ polypeptide.

The invention also includes a method for identifying an antibacterial agent which method entails: (a) contacting an S-yacM or S-yqeJ polypeptide, or homolog or ortholog thereof, with a test compound; (b) detecting binding of the test compound to the polypeptide or homolog or ortholog; and, optionally, (c) determining whether a test compound that binds to the polypeptide or homolog or ortholog (i.e., a candidate antibacterial compound) inhibits growth of bacteria, relative to growth of bacteria cultured in the absence of the test compound that binds to the polypeptide or homolog or ortholog, as an indication that the test compound is an antibacterial agent.

In an alternative method, compounds that decrease the expression of the yacM or yqeJ polypeptide are identified in an in vivo assay. Such compounds can be used as antibacterial agents. To discover such compounds, cells that express a yacM or yqeJ polypeptide (e.g., genetically engineered cells) are cultured, exposed to a test compound (or a mixture of test compounds), and the level of expression or activity is compared with the level of yacM or yqeJ polypeptide expression or activity in cells that are otherwise identical but that have not been exposed to the test compound(s). Many standard quantitative assays of gene expression can be utilized in this aspect of the invention.

To identify compounds that modulate expression of a yacM or yqeJ polypeptide, the test compound(s) can be added at varying concentrations to the culture medium of cells that express a yacM or yqeJ polypeptide, as described herein. Such test compounds can include small molecules (typically, non-protein, non-polysaccharide chemical entities), polypeptides, and nucleic acids. The expression of the yacM or yqeJ polypeptide is then measured, for example, by Northern blot, PCR analysis, or RNAse protection analyses using a nucleic acid molecule of the invention as a probe. The level of expression in the presence of the test molecule, compared with the level of expression in its absence, will indicate whether or not the test molecule alters the expression of the yacM or yqeJ polypeptide. Because the yacM and yqeJ polypeptides thereof are essential for survival, test compounds that inhibit the expression and/or function of the yacM or yqeJ polypeptide will inhibit growth of, or kill, the cells that express such polypeptides.

Test compounds can also be assayed for their ability to inhibit cell growth in an overexpression/underexpression screen. In such an assay, the wild-type yacM or yqeJ gene in a cell is replaced with a yacM or yqeJ gene that is under the control of a regulated promoter. By adjusting the level of inducer added to the cell culture, one can produce (i) a cell that expresses more yacM or yqeJ protein than does the wild-type cell (i.e., overexpression) and (ii) a cell that expresses less yacM or yqeJ protein than does the wild-type cell (i.e., underexpression). By adjusting the level of inducer, the level of yacM or yqeJ expression can be increased or decreased (e.g., by at least 25%, 50%, 100%, 200%, or even 500% or greater). Optimally, the inducer is added at low levels to the cells used for underexpression, such that the cells are barely able to grow. Such cells are growth-limited by yacM or yqeJ protein activity, and should therefore be especially sensitive to yacM or yqeJ inhibitors. The cells used for underexpression can be used to detect inhibitors. A comparison with inhibition of the cells used for overexpression, or with the wild-type strain, which should be more resistant than the cells used for underexpression, provides an indication of the specificity of the test compound.

In various cell-based methods for identifying polypeptides that bind yacM or yqeJ polypeptides, the conventional two-hybrid assays of protein/protein interactions can be used (See e.g., Chien et al., Proc. Natl. Acad. Sci. USA, 88:9578, 1991; Fields et al., U.S. Pat. No. 5,283,173; Fields and Song, Nature, 340:245, 1989; Le Douarin et al., Nucleic Acids Research, 23:876, 1995; Vidal et al., Proc. Natl. Acad. Sci. USA, 93:10315–10320, 1996; and White, Proc. Natl. Acad. Sci. USA, 93:10001–10003, 1996). Generally, the two-hybrid methods involve in vivo reconstitution of two separable domains of a transcription factor in a cell. One fusion protein contains the yacM or yqeJ polypeptide fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the essential polypeptide to the test polypeptide (i.e., a candidate antibacterial compound) reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

Many of the methods described above can be used for high throughput screening of numerous test compounds to identify candidate antibacterial (or anti-bacterial) agents.

Having identified a test compound as a candidate antibacterial agent, the candidate antibacterial agent can be further tested for inhibition of bacterial growth in vitro or in vivo (e.g., using an animal, e.g., rodent, model system) if desired. Using other, art-known variations of such methods, one can test the ability of a nucleic acid (e.g., DNA or RNA) used as the test compound to bind yacM or yqeJ.

In vitro, further testing can be accomplished by means known to those in the art such as an enzyme inhibition assay or a whole-cell bacterial growth inhibition assay. For example, an agar dilution assay identifies a substance that inhibits bacterial growth. Microtiter plates are prepared with serial dilutions of the test compound, adding to the preparation a given amount of growth substrate, and providing a preparation of bacteria. Inhibition of bacterial growth is determined, for example, by observing changes in optical densities of the bacterial cultures.

Inhibition of bacterial growth is demonstrated, for example, by comparing (in the presence and absence of a test compound) the rate of growth or the absolute growth of bacterial cells. Inhibition includes a reduction of one of the above measurements by at least 20%. Particularly potent test compounds may further reduce the growth rate (e.g., by at least 25%, 30%, 40%, 50%, 75%, 80%, or 90%).

Rodent (e.g., murine) and rabbit animal models of bacterial infections are known to those of skill in the art, and such animal model systems are accepted for screening antibacterial agents as an indication of their therapeutic efficacy in human patients. In a typical in vivo assay, an animal is infected with a pathogenic strain of bacteria, e.g., by inhalation of bacteria such as *Streptococcus pneumoniae*, and conventional methods and criteria are used to diagnose the mammal as being afflicted with a bacterial infection. The candidate antibacterial agent then is administered to the mammal at a dosage of 1–100 mg/kg of body weight, and the mammal is monitored for signs of amelioration of disease. Alternatively, the test compound can be administered to the mammal prior to infecting the mammal with the bacteria, and the ability of the treated mammal to resist infection is measured. Of course, the results obtained in the presence of the test compound should be compared with results in control animals, which are not treated with the test compound. Administration of candidate antibacterial agents to the mammal can be carried out as described herein, for example.

Medicinal Chemistry

Once a compound that interacts with yacM or yqeJ has been identified, principles of standard medicinal chemistry can be used, if desired, to produce derivatives of the compound, e.g., derivatives that have improved properties as antibacterial agents. The moieties that are responsible for a compound's activity can be revealed by examining its structure-activity relationships (SAR). Specifically, a person of ordinary skill in the art of chemistry could modify a moiety of the compound to study the effects of the modification on the potency of the compound and thereby produce derivatives of the compound having increased potency (See, e.g., Nagarajan et al., Antibiot. 41:430–438). For example, chemical modifications such as N-acylation, esterification, hydroxylation, alkylation, amination, amidation, oxidation, or reduction can be made. Such chemical modifications can be made according to conventional methods (See, e.g., Wade, Organic Chemistry, Prentice-Hall, Inc., New Jersey, 1987). If structural information of the compound and its interaction with a yacM or yqeJ polypeptide or gene are available, derivatives of the inhibitor can be generated and optimized virtually by using molecular modeling software and conventional methods. Such software is commercially available (e.g., from Tripos Inc., Molecular Simulations, Inc., and MDL Information Systems, Inc).

Pharmaceutical Formulations

Treatment includes administering a pharmaceutically effective amount of a composition containing an antibacterial agent to an organism in need of such treatment, thereby inhibiting bacterial growth in the organism. Such a composition typically contains from about 0.1 to 90% by weight (such as 1 to 20% or 1 to 10%) of an antibacterial agent of the invention in a pharmaceutically acceptable carrier.

Solid formulations of the compositions for oral administration may contain suitable carriers or excipients, such as cornstarch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, sodium starch glycolate and alginic acid. Tablet binders that may be used include acacia, methylcellulose, sodium carboxymethylcellulose, polyvinylpyrrolidone (POVIDONE™), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the organism to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water-soluble versions of the compounds may be administered by the drip method, whereby a pharmaceutical formulation containing the antibacterial agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antibacterial agent in each pharmaceutical formulation varies according to the formulation itself and the therapeutic effect desired in the specific pathologies and correlated therapeutic regimens. Appropriate dosages of the antibacterial agents can be readily determined by those of ordinary skill in the art by monitoring the organism for signs of disease amelioration or inhibition, and increasing or decreasing the dosage and/or frequency of treatment as desired. The optimal amount of the antibacterial compound used for treatment of conditions caused by or contributed to by bacterial infection may depend upon the manner of administration, the age and the body weight of the subject, and the condition of the subject to be treated. Generally, the antibacterial compound is administered at a dosage of 1 to 100 mg/kg of body weight, and typically at a dosage of 1 to 10 mg/kg of body weight.

Other Embodiments

The methods of the invention can be practiced with various fragments, variants, analogs, and derivatives of the yacM and yqeJ polypeptides described above that retain one or more of the biological activities of the yacM and yqeJ polypeptides, including naturally-occurring and non-naturally-occurring variants. Compared with the naturally-occurring essential gene sequences depicted herein, the nucleic acid sequences encoding variants may have a substitution, deletion, or addition of one or more nucleotides. The preferred variants retain a function of yacM or yqeJ polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, other art-known assays to detect interactions of test compounds with proteins, or to detect inhibition of bacterial growth also can be used with the essential genes, gene products, and homologs and orthologs thereof.

What is claimed is:

1. A method for determining whether a test compound is a candidate antibacterial compound, the method comprising:
   (a) contacting an S-yacM (SEQ ID NO.:2) or an S-yqeJ (SEQ ID NO.:5) polypeptide with the test compound; and
   (b) detecting interaction of the test compound with the S-yacM or S-yqeJ polypeptide, wherein an interaction indicates that the test compound is a candidate antibacterial compound.

2. A method of claim 1, further comprising:
   (c) determining whether the candidate antibacterial compound inhibits growth of bacteria, relative to growth of bacteria cultured in the absence of the candidate antibacterial compound, wherein inhibition of growth indicates that the candidate antibacterial compound is an antibacterial agent.

3. A composition comprising an antibacterial agent identified by the method of claim 2, and a pharmaceutically acceptable excipient.

4. A method for determining whether a test compound is an antibacterial agent, the method comprising:
   (a) contacting an S-yacM (SEQ ID NO.:2) or an S-yqeJ (SEQ ID NO.:5) polypeptide with a test compound;
   (b) detecting a decrease in biochemical activity of the polypeptide contacted with the test compound, wherein a decrease in biochemical activity indicates that the compound is a candidate antibacterial compound; and
   (c) determining whether the candidate antibacterial compound inhibits growth of bacteria, relative to growth of bacteria cultured in the absence of the candidate antibacterial compound, wherein inhibition of growth indicates that the candidate antibacterial compound is an antibacterial agent.

5. The method of claim 1, wherein the polypeptide is an S-yacM (SEQ ID NO.:2) polypeptide.

6. The method of claim 1, wherein the polypeptide is an S-yqeJ (SEQ ID NO.:5) polypeptide.

7. The method of claim 4, wherein the polypeptide is an S-yacM (SEQ ID NO.:2) polypeptide.

8. The method of claim 4, wherein the polypeptide is an S-yqeJ (SEQ ID NO.:5) polypeptide.

* * * * *

SEQUENCE LISTING

<160> NUMBER OF SEQ ID NOS: 28

<210> SEQ ID NO 1
<211> LENGTH: 708
<212> TYPE: DNA
<213> ORGANISM: Streptococcus pneumoniae
<220> FEATURE:
<221> NAME/KEY: CDS
<222> LOCATION: (1)...(705)

<400> SEQUENCE: 1

```
atg att tat gca gga att ctt gcc ggt gga act ggc aca cgc atg ggg      48
Met Ile Tyr Ala Gly Ile Leu Ala Gly Gly Thr Gly Thr Arg Met Gly
  1               5                  10                  15 atc agt aac ttg cca aaa caa ttt tta gag cta ggt gat cga cct att      96
Ile Ser Asn Leu Pro Lys Gln Phe Leu Glu Leu Gly Asp Arg Pro Ile
             20                  25                  30 ttg att cat aca att gaa aaa ttt gtc ttg gag cca agt att gaa aaa     144
Leu Ile His Thr Ile Glu Lys Phe Val Leu Glu Pro Ser Ile Glu Lys
         35                  40                  45 att gta gtt ggt gtt cat gga gac tgg gtt tct cat gca gaa gat ctt     192
Ile Val Val Gly Val His Gly Asp Trp Val Ser His Ala Glu Asp Leu
     50                  55                  60 gta gat aaa tat ctt cct ctt tat aag gaa cgt atc atc att aca aag     240
Val Asp Lys Tyr Leu Pro Leu Tyr Lys Glu Arg Ile Ile Ile Thr Lys
 65                  70                  75                  80 ggt ggt gct gac cgc aat aca agt att aag aac atc att gaa gcc att     288
Gly Gly Ala Asp Arg Asn Thr Ser Ile Lys Asn Ile Ile Glu Ala Ile
                 85                  90                  95 gat gct tat cgt ccg ctt act cca gag gat atc gtt gtt acc cac gat     336
Asp Ala Tyr Arg Pro Leu Thr Pro Glu Asp Ile Val Val Thr His Asp
            100                 105                 110 tct gtt cgt cca ttt att aca ctt cgc atg att cag gac aat atc caa     384
Ser Val Arg Pro Phe Ile Thr Leu Arg Met Ile Gln Asp Asn Ile Gln
        115                 120                 125 ctt gcc caa aat cat gac gca gtg gac aca gtg gta gaa gcg gtt gat     432
Leu Ala Gln Asn His Asp Ala Val Asp Thr Val Val Glu Ala Val Asp
    130                 135                 140 act atc gtt gaa agt acc aat ggt caa ttt att aca gat att cca aat     480
Thr Ile Val Glu Ser Thr Asn Gly Gln Phe Ile Thr Asp Ile Pro Asn
145                 150                 155                 160 cgt gct cac ctt tat caa gga caa aca cct caa aca ttc cgt tgc aag     528
```

```
                Arg Ala His Leu Tyr Gln Gly Gln Thr Pro Gln Thr Phe Arg Cys Lys
                                165                 170                 175 gac ttc atg gac ctt tat gga tct ctt tct gat gaa gag aag gaa atc           576
Asp Phe Met Asp Leu Tyr Gly Ser Leu Ser Asp Glu Glu Lys Glu Ile
            180                 185                 190 ttg aca gat gca tgt aaa atc ttt gtg atc aaa gga aaa gat gtg gct           624
Leu Thr Asp Ala Cys Lys Ile Phe Val Ile Lys Gly Lys Asp Val Ala
        195                 200                 205 ttg gcc aaa ggt gaa tac tca aat ctg aag att aca acc gta aca gat           672
Leu Ala Lys Gly Glu Tyr Ser Asn Leu Lys Ile Thr Thr Val Thr Asp
    210                 215                 220 ttg aag att gca aaa agt atg att gag aaa gac tag                           708
Leu Lys Ile Ala Lys Ser Met Ile Glu Lys Asp
225                 230                 235
```

<210> SEQ ID NO 2
<211> LENGTH: 235
<212> TYPE: PRT
<213> ORGANISM: Streptococcus pneumoniae

<400> SEQUENCE: 2

```
Met Ile Tyr Ala Gly Ile Leu Ala Gly Gly Thr Gly Thr Arg Met Gly
 1               5                   10                  15

Ile Ser Asn Leu Pro Lys Gln Phe Leu Glu Leu Gly Asp Arg Pro Ile
            20                  25                  30

Leu Ile His Thr Ile Glu Lys Phe Val Leu Glu Pro Ser Ile Glu Lys
        35                  40                  45

Ile Val Val Gly Val His Gly Asp Trp Val Ser His Ala Glu Asp Leu
    50                  55                  60

Val Asp Lys Tyr Leu Pro Leu Tyr Lys Glu Arg Ile Ile Ile Thr Lys
65                  70                  75                  80

Gly Gly Ala Asp Arg Asn Thr Ser Ile Lys Asn Ile Ile Glu Ala Ile
                85                  90                  95

Asp Ala Tyr Arg Pro Leu Thr Pro Glu Asp Ile Val Val Thr His Asp
            100                 105                 110

Ser Val Arg Pro Phe Ile Thr Leu Arg Met Ile Gln Asp Asn Ile Gln
        115                 120                 125

Leu Ala Gln Asn His Asp Ala Val Asp Thr Val Glu Ala Val Asp
    130                 135                 140

Thr Ile Val Glu Ser Thr Asn Gly Gln Phe Ile Thr Asp Ile Pro Asn
145                 150                 155                 160

Arg Ala His Leu Tyr Gln Gly Gln Thr Pro Gln Thr Phe Arg Cys Lys
                165                 170                 175

Asp Phe Met Asp Leu Tyr Gly Ser Leu Ser Asp Glu Glu Lys Glu Ile
            180                 185                 190

Leu Thr Asp Ala Cys Lys Ile Phe Val Ile Lys Gly Lys Asp Val Ala
        195                 200                 205

Leu Ala Lys Gly Glu Tyr Ser Asn Leu Lys Ile Thr Thr Val Thr Asp
    210                 215                 220

Leu Lys Ile Ala Lys Ser Met Ile Glu Lys Asp
225                 230                 235
```

<210> SEQ ID NO 3
<211> LENGTH: 708
<212> TYPE: DNA
<213> ORGANISM: Streptococcus pneumoniae

<400> SEQUENCE: 3

-continued

```
ctagtctttc tcaatcatac tttttgcaat cttcaaatct gttacggttg taatcttcag      60
atttgagtat tcacctttgg ccaaagccac atcttttcct ttgatcacaa agattttaca     120
tgcatctgtc aagatttcct tctcttcatc agaaagagat ccataaaggt ccatgaagtc     180
cttgcaacgg aatgtttgag gtgtttgtcc ttgataaagg tgagcacgat ttggaatatc     240
tgtaataaat tgaccattgg tactttcaac gatagtatca accgcttcta ccactgtgtc     300
cactgcgtca tgattttggg caagttggat attgtcctga atcatgcgaa gtgtaataaa     360
tggacgaaca gaatcgtggg taacaacgat atcctctgga gtaagcggac gataagcatc     420
aatggcttca atgatgttct taatacttgt attgcggtca gcaccaccct ttgtaatgat     480
gatacgttcc ttataaagag gaagatattt atctacaaga tcttctgcat gagaaaccca     540
gtctccatga acaccaacta caatttttc aatacttggc tccaagacaa attttcaat      600 tgtatgaatc aaaataggtc gatcacctag ctctaaaaat tgttttggca agttactgat     660
ccccatgcgt gtgccagttc caccggcaag aattcctgca taaatcat                 708
```

<210> SEQ ID NO 4
<211> LENGTH: 630
<212> TYPE: DNA
<213> ORGANISM: Streptococcus pneumoniae
<220> FEATURE:
<221> NAME/KEY: CDS
<222> LOCATION: (1)...(627)

<400> SEQUENCE: 4

```
atg aca atc gaa cta ttg act ccc ttt acc aag gta gag ttg gag cca        48
Met Thr Ile Glu Leu Leu Thr Pro Phe Thr Lys Val Glu Leu Glu Pro
1               5                   10                  15 gaa atc aag gag aaa aaa cgc aaa caa gtt ggg att tta ggg ggg aat        96
Glu Ile Lys Glu Lys Lys Arg Lys Gln Val Gly Ile Leu Gly Gly Asn
                20                  25                  30 ttt aac cct gtt cac aat gcc cat ctc att gtt gcg gat caa gta cgg       144
Phe Asn Pro Val His Asn Ala His Leu Ile Val Ala Asp Gln Val Arg
            35                  40                  45 caa cag ttg gga ctg gat caa gtt ctt ctc atg cct gaa tac caa cct       192
Gln Gln Leu Gly Leu Asp Gln Val Leu Leu Met Pro Glu Tyr Gln Pro
        50                  55                  60 cct cac gtt gat aaa aag gaa acc atc cct gaa cac cat cgt ctc aag       240
Pro His Val Asp Lys Lys Glu Thr Ile Pro Glu His His Arg Leu Lys
65                  70                  75                  80 atg ctt gag ttg gca att gag ggg att gac ggc cta gtc att gaa acc       288
Met Leu Glu Leu Ala Ile Glu Gly Ile Asp Gly Leu Val Ile Glu Thr
                85                  90                  95 att gag ttg gag cgc aag ggt att tcc tac acc tac gat acc atg aag       336
Ile Glu Leu Glu Arg Lys Gly Ile Ser Tyr Thr Tyr Asp Thr Met Lys
            100                 105                 110 att ttg aca gag aag aat cca gat acg gat tat tac ttt atc atc ggt       384
Ile Leu Thr Glu Lys Asn Pro Asp Thr Asp Tyr Tyr Phe Ile Ile Gly
        115                 120                 125 gcc gac atg gtt gac tat ctg cct aag tgg tac cga att gat gaa ctg       432
Ala Asp Met Val Asp Tyr Leu Pro Lys Trp Tyr Arg Ile Asp Glu Leu
    130                 135                 140 gtt gac atg gtt cag ttt gtg ggg gtt cag cgt cca cgc tac aag gta       480
Val Asp Met Val Gln Phe Val Gly Val Gln Arg Pro Arg Tyr Lys Val
145                 150                 155                 160 ggg act tcc tat cca gtt atc tgg gtg gac gta ccg ctc atg gat atc       528
Gly Thr Ser Tyr Pro Val Ile Trp Val Asp Val Pro Leu Met Asp Ile
                165                 170                 175
```

| | | | | | | | | | | | | | | |
|---|---|---|---|---|---|---|---|---|---|---|---|---|---|---|
| tcg | tcc | agc | atg | gtg | cgg | gac | ttc | ctt | gcc | caa | ggt | cgg | aaa | ccc | aac | 576 |
| Ser | Ser | Ser | Met | Val | Arg | Asp | Phe | Leu | Ala | Gln | Gly | Arg | Lys | Pro | Asn | |
| | | 180 | | | | | 185 | | | | | 190 | | | |
| ttt | ctc | cta | cct | cag | cca | gtg | cta | gac | tac | atc | gag | aag | gag | ggg | ctc | 624 |
| Phe | Leu | Leu | Pro | Gln | Pro | Val | Leu | Asp | Tyr | Ile | Glu | Lys | Glu | Gly | Leu | |
| | | 195 | | | | | 200 | | | | | 205 | | | |
| tac | tga | | | | | | | | | | | | | | | 630 |
| Tyr | | | | | | | | | | | | | | | | |

<210> SEQ ID NO 5
<211> LENGTH: 209
<212> TYPE: PRT
<213> ORGANISM: Streptococcus pneumoniae

<400> SEQUENCE: 5

Met Thr Ile Glu Leu Leu Thr Pro Phe Thr Lys Val Glu Leu Glu Pro
 1               5                  10                  15

Glu Ile Lys Glu Lys Arg Lys Gln Val Gly Ile Leu Gly Gly Asn
             20                  25                  30

Phe Asn Pro Val His Asn Ala His Leu Ile Val Ala Asp Gln Val Arg
         35                  40                  45

Gln Gln Leu Gly Leu Asp Gln Val Leu Leu Met Pro Glu Tyr Gln Pro
     50                  55                  60

Pro His Val Asp Lys Lys Glu Thr Ile Pro Glu His Arg Leu Lys
 65                  70                  75                  80

Met Leu Glu Leu Ala Ile Glu Gly Ile Asp Gly Leu Val Ile Glu Thr
                 85                  90                  95

Ile Glu Leu Glu Arg Lys Gly Ile Ser Tyr Thr Tyr Asp Thr Met Lys
            100                 105                 110

Ile Leu Thr Glu Lys Asn Pro Asp Thr Asp Tyr Tyr Phe Ile Ile Gly
        115                 120                 125

Ala Asp Met Val Asp Tyr Leu Pro Lys Trp Tyr Arg Ile Asp Glu Leu
    130                 135                 140

Val Asp Met Val Gln Phe Val Gly Val Gln Arg Pro Arg Tyr Lys Val
145                 150                 155                 160

Gly Thr Ser Tyr Pro Val Ile Trp Val Asp Val Pro Leu Met Asp Ile
                165                 170                 175

Ser Ser Ser Met Val Arg Asp Phe Leu Ala Gln Gly Arg Lys Pro Asn
            180                 185                 190

Phe Leu Leu Pro Gln Pro Val Leu Asp Tyr Ile Glu Lys Glu Gly Leu
        195                 200                 205

Tyr

<210> SEQ ID NO 6
<211> LENGTH: 630
<212> TYPE: DNA
<213> ORGANISM: Streptococcus pneumoniae

<400> SEQUENCE: 6
tcagtagagc ccctccttct cgatgtagtc tagcactggc tgaggtagga gaaagttggg    60
tttccgacct tgggcaagga agtcccgcac catgctggac gagatatcca tgagcggtac   120
gtccacccag ataactggat aggaagtccc taccttgtag cgtggacgct gaacccccac   180
aaactgaacc atgtcaacca gttcatcaat tcggtaccac ttaggcagat agtcaaccat   240
gtcggcaccg atgataaagt aataatccgt atctggattc ttctctgtca aaatcttcat   300

```
ggtatcgtag gtgtaggaaa taccccttgcg ctccaactca atggtttcaa tgactaggcc    360
gtcaatcccc tcaattgcca actcaagcat cttgagacga tggtgttcag ggatggtttc    420 cttttttatca acgtgaggag gttggtattc aggcatgaga agaacttgat ccagtcccaa   480
ctgttgccgt acttgatccg caacaatgag atgggcattg tgaacagggt taaaattccc    540
ccctaaaatc ccaacttgtt tgcgtttttt ctccttgatt tctggctcca actctacctt    600
ggtaaaggga gtcaatagtt cgattgtcat                                     630
```

```
<210> SEQ ID NO 7
<211> LENGTH: 699
<212> TYPE: DNA
<213> ORGANISM: Bacillus subtilis
<220> FEATURE:
<221> NAME/KEY: CDS
<222> LOCATION: (1)...(696)

<400> SEQUENCE: 7
```

```
atg agt tat gat gtg gtg att cct gca gcc gga cag gga aag cgg atg       48
Met Ser Tyr Asp Val Val Ile Pro Ala Ala Gly Gln Gly Lys Arg Met
 1               5                  10                  15 aag gca ggg aga aat aaa ctg ttc att gag ctg aag gga gac ccg gtg       96
Lys Ala Gly Arg Asn Lys Leu Phe Ile Glu Leu Lys Gly Asp Pro Val
                 20                  25                  30 atc ata cac acg tta aga gtg ttt gac agc cac cgg cag tgc gat aaa      144
Ile Ile His Thr Leu Arg Val Phe Asp Ser His Arg Gln Cys Asp Lys
             35                  40                  45 atc att ttg gtg att aac gag cag gag cgg gag cac ttt cag caa ttg      192
Ile Ile Leu Val Ile Asn Glu Gln Glu Arg Glu His Phe Gln Gln Leu
         50                  55                  60 ctg tcc gat tac ccg ttt caa act tca att gag ctt gtt gca ggc gga      240
Leu Ser Asp Tyr Pro Phe Gln Thr Ser Ile Glu Leu Val Ala Gly Gly
 65                  70                  75                  80 gat gag cga cag cac agt gtg tat aag ggg ctg aaa gcc gta aag cag      288
Asp Glu Arg Gln His Ser Val Tyr Lys Gly Leu Lys Ala Val Lys Gln
                 85                  90                  95 gaa aag att gtc ctt gta cat gac ggt gcc cgt cca ttt ata aaa cat      336
Glu Lys Ile Val Leu Val His Asp Gly Ala Arg Pro Phe Ile Lys His
                100                 105                 110 gaa caa att gac gaa ctg atc gca gag gcg gaa cag aca gga gcg gcc      384
Glu Gln Ile Asp Glu Leu Ile Ala Glu Ala Glu Gln Thr Gly Ala Ala
            115                 120                 125 atc ctt gct gtt ccg gta aaa gat acg att aaa cgc gtt caa gat tta      432
Ile Leu Ala Val Pro Val Lys Asp Thr Ile Lys Arg Val Gln Asp Leu
        130                 135                 140 caa gtc agt gag acg att gaa cgt tca agc ttg tgg gct gtc caa acg      480
Gln Val Ser Glu Thr Ile Glu Arg Ser Ser Leu Trp Ala Val Gln Thr
145                 150                 155                 160 cca caa gct ttt cgt ctt tct tta ttg atg aag gct cac gct gag gcc      528
Pro Gln Ala Phe Arg Leu Ser Leu Leu Met Lys Ala His Ala Glu Ala
                165                 170                 175 gag cgc aag gga ttt tta ggg acg gat gac gcc agc ctc gtt gaa cag      576
Glu Arg Lys Gly Phe Leu Gly Thr Asp Asp Ala Ser Leu Val Glu Gln
            180                 185                 190 atg gag ggc ggt tcg gtc cgt gtt gta gaa ggc agc tat aca aat att      624
Met Glu Gly Gly Ser Val Arg Val Val Glu Gly Ser Tyr Thr Asn Ile
        195                 200                 205 aag ctg acg acg cca gac gat ttg acg tca gct gaa gct atc atg gaa      672
Lys Leu Thr Thr Pro Asp Asp Leu Thr Ser Ala Glu Ala Ile Met Glu
    210                 215                 220
```

```
tca gaa agt ggg aat aaa cat gtt tag                                           699
Ser Glu Ser Gly Asn Lys His Val
225                 230
```

<210> SEQ ID NO 8
<211> LENGTH: 232
<212> TYPE: PRT
<213> ORGANISM: Bacillus subtilis

<400> SEQUENCE: 8

```
Met Ser Tyr Asp Val Val Ile Pro Ala Ala Gly Gln Gly Lys Arg Met
  1               5                  10                  15

Lys Ala Gly Arg Asn Lys Leu Phe Ile Glu Leu Lys Gly Asp Pro Val
                 20                  25                  30

Ile Ile His Thr Leu Arg Val Phe Asp Ser His Arg Gln Cys Asp Lys
             35                  40                  45

Ile Ile Leu Val Ile Asn Glu Gln Arg Glu His Phe Gln Gln Leu
         50                  55                  60

Leu Ser Asp Tyr Pro Phe Gln Thr Ser Ile Glu Leu Val Ala Gly Gly
 65                  70                  75                  80

Asp Glu Arg Gln His Ser Val Tyr Lys Gly Leu Lys Ala Val Lys Gln
                 85                  90                  95

Glu Lys Ile Val Leu Val His Asp Gly Ala Arg Pro Phe Ile Lys His
            100                 105                 110

Glu Gln Ile Asp Glu Leu Ile Ala Glu Ala Gln Thr Gly Ala Ala
            115                 120                 125

Ile Leu Ala Val Pro Val Lys Asp Thr Ile Lys Arg Val Gln Asp Leu
        130                 135                 140

Gln Val Ser Glu Thr Ile Glu Arg Ser Ser Leu Trp Ala Val Gln Thr
145                 150                 155                 160

Pro Gln Ala Phe Arg Leu Ser Leu Leu Met Lys Ala His Ala Glu Ala
                165                 170                 175

Glu Arg Lys Gly Phe Leu Gly Thr Asp Asp Ala Ser Leu Val Glu Gln
            180                 185                 190

Met Glu Gly Gly Ser Val Arg Val Val Glu Gly Ser Tyr Thr Asn Ile
            195                 200                 205

Lys Leu Thr Thr Pro Asp Asp Leu Thr Ser Ala Glu Ala Ile Met Glu
        210                 215                 220

Ser Glu Ser Gly Asn Lys His Val
225                 230
```

<210> SEQ ID NO 9
<211> LENGTH: 699
<212> TYPE: DNA
<213> ORGANISM: Bacillus subtilis

<400> SEQUENCE: 9

```
ctaaacatgt ttattcccac tttctgattc catgatagct tcagctgacg tcaaatcgtc    60
tggcgtcgtc agcttaatat tgtatagct gccttctaca acacggaccg aaccgccctc   120
catctgttca acgaggctgg cgtcatccgt ccctaaaaat cccttgcgct cggcctcagc   180
gtgagccttc atcaataaag aaagacgaaa agcttgtggc gtttggacag cccacaagct   240
tgaacgttca atcgtctcac tgacttgtaa atcttgaacg cgtttaatcg tatcttttac   300
cggaacagca aggatggccg ctcctgtctg ttccgcctct gcgatcagtt cgtcaatttg   360
ttcatgtttt ataaatggac gggcaccgtc atgtacaagg acaatctttt cctgctttac   420
```

```
ggctttcagc ccttatacac actgtgctg tcgctcatct ccgcctgcaa caagctcaat    480
tgaagtttga acgggtaat cggacagcaa ttgctgaaag tgctcccgct cctgctcgtt    540
aatcaccaaa atgattttat cgcactgccg gtggctgtca acactctta acgtgtgtat    600 gatcaccggg tctcccttca gctcaatgaa cagtttattt ctccctgcct tcatccgctt    660
tccctgtccg gctgcaggaa tcaccacatc ataactcat                          699

<210> SEQ ID NO 10
<211> LENGTH: 711
<212> TYPE: DNA
<213> ORGANISM: Escherichia coli
<220> FEATURE:
<221> NAME/KEY: CDS
<222> LOCATION: (1)...(708)

<400> SEQUENCE: 10 atg gca acc act cat ttg gat gtt tgc gcc gtg gtt ccg gcg gcc gga    48
Met Ala Thr Thr His Leu Asp Val Cys Ala Val Val Pro Ala Ala Gly
1               5                   10                  15 ttt ggc cgt cga atg caa acg gaa tgt cct aag caa tat ctc tca atc    96
Phe Gly Arg Arg Met Gln Thr Glu Cys Pro Lys Gln Tyr Leu Ser Ile
            20                  25                  30 ggt aat caa acc att ctt gaa cac tcg gtg cat gcg ctg ctg gcg cat    144
Gly Asn Gln Thr Ile Leu Glu His Ser Val His Ala Leu Leu Ala His
        35                  40                  45 ccc cgg gtg aaa cgt gtc gtc att gcc ata agt cct ggc gat agc cgt    192
Pro Arg Val Lys Arg Val Val Ile Ala Ile Ser Pro Gly Asp Ser Arg
50                  55                  60 ttt gca caa ctt cct ctg gcg aat cat ccg caa atc acc gtt gta gat    240
Phe Ala Gln Leu Pro Leu Ala Asn His Pro Gln Ile Thr Val Val Asp
65                  70                  75                  80 ggc ggt gat gag cgt gcc gat tcc gtg ctg gca ggt ctg aaa gcc gct    288
Gly Gly Asp Glu Arg Ala Asp Ser Val Leu Ala Gly Leu Lys Ala Ala
                85                  90                  95 ggc gac gcg cag tgg gta ttg gtg cat gac gcc gct cgt cct tgt ttg    336
Gly Asp Ala Gln Trp Val Leu Val His Asp Ala Ala Arg Pro Cys Leu
            100                 105                 110 cat cag gat gac ctc gcg cga ttg ttg gcg ttg agc gaa acc agc cgc    384
His Gln Asp Asp Leu Ala Arg Leu Leu Ala Leu Ser Glu Thr Ser Arg
        115                 120                 125 acg ggg ggg atc ctc gcc gca cca gtg cgc gat act atg aaa cgt gcc    432
Thr Gly Gly Ile Leu Ala Ala Pro Val Arg Asp Thr Met Lys Arg Ala
    130                 135                 140 gaa ccg ggc aaa aat gcc att gct cat acc gtt gat cgc aac ggc tta    480
Glu Pro Gly Lys Asn Ala Ile Ala His Thr Val Asp Arg Asn Gly Leu
145                 150                 155                 160 tgg cac gcg ctg acg ccg caa ttt ttc cct cgt gag ctg tta cat gac    528
Trp His Ala Leu Thr Pro Gln Phe Phe Pro Arg Glu Leu Leu His Asp
                165                 170                 175 tgt ctg acg cgc gct cta aat gaa ggc gcg act att acc gac gaa gcc    576
Cys Leu Thr Arg Ala Leu Asn Glu Gly Ala Thr Ile Thr Asp Glu Ala
            180                 185                 190 tcg gcg ctg gaa tat tgc gga ttc cat cct cag ttg gtc gaa ggc cgt    624
Ser Ala Leu Glu Tyr Cys Gly Phe His Pro Gln Leu Val Glu Gly Arg
        195                 200                 205 gcg gat aac att aaa gtc acg cgc ccg gaa gat ttg gca ctg gcc gag    672
Ala Asp Asn Ile Lys Val Thr Arg Pro Glu Asp Leu Ala Leu Ala Glu
    210                 215                 220 ttt tac ctc acc cga acc atc cat cag gag aat aca taa                 711
Phe Tyr Leu Thr Arg Thr Ile His Gln Glu Asn Thr
```

<210> SEQ ID NO 11
<211> LENGTH: 236
<212> TYPE: PRT
<213> ORGANISM: Escherichia coli

<400> SEQUENCE: 11

| Met | Ala | Thr | Thr | His | Leu | Asp | Val | Cys | Ala | Val | Pro | Ala | Ala | Gly |
| 1 | | | | 5 | | | | | 10 | | | | | 15 |

Phe Gly Arg Arg Met Gln Thr Glu Cys Pro Lys Gln Tyr Leu Ser Ile
            20                  25                  30

Gly Asn Gln Thr Ile Leu Glu His Ser Val His Ala Leu Leu Ala His
        35                  40                  45

Pro Arg Val Lys Arg Val Val Ile Ala Ile Ser Pro Gly Asp Ser Arg
    50                  55                  60

Phe Ala Gln Leu Pro Leu Ala Asn His Pro Gln Ile Thr Val Val Asp
65                  70                  75                  80

Gly Gly Asp Glu Arg Ala Asp Ser Val Leu Ala Gly Leu Lys Ala Ala
                85                  90                  95

Gly Asp Ala Gln Trp Val Leu Val His Asp Ala Ala Arg Pro Cys Leu
            100                 105                 110

His Gln Asp Asp Leu Ala Arg Leu Leu Ala Leu Ser Glu Thr Ser Arg
        115                 120                 125

Thr Gly Gly Ile Leu Ala Ala Pro Val Arg Asp Thr Met Lys Arg Ala
    130                 135                 140

Glu Pro Gly Lys Asn Ala Ile Ala His Thr Val Asp Arg Asn Gly Leu
145                 150                 155                 160

Trp His Ala Leu Thr Pro Gln Phe Phe Pro Arg Glu Leu Leu His Asp
                165                 170                 175

Cys Leu Thr Arg Ala Leu Asn Glu Gly Ala Thr Ile Thr Asp Glu Ala
            180                 185                 190

Ser Ala Leu Glu Tyr Cys Gly Phe His Pro Gln Leu Val Glu Gly Arg
        195                 200                 205

Ala Asp Asn Ile Lys Val Thr Arg Pro Glu Asp Leu Ala Leu Ala Glu
    210                 215                 220

Phe Tyr Leu Thr Arg Thr Ile His Gln Glu Asn Thr
225                 230                 235

<210> SEQ ID NO 12
<211> LENGTH: 711
<212> TYPE: DNA
<213> ORGANISM: Escherichia coli

<400> SEQUENCE: 12

| ttatgtattc | tcctgatgga | tggttcgggt | gaggtaaaac | tcggccagtg | ccaaatcttc | 60 |
| cgggcgcgtg | actttaatgt | tatccgcacg | gccttcgacc | aactgaggat | ggaatccgca | 120 |
| atattccagc | gccgaggctt | cgtcggtaat | agtcgcgcct | tcatttagag | cgcgcgtcag | 180 |
| acagtcatgt | aacagctcac | gagggaaaaa | ttgcggcgtc | agcgcgtgcc | ataagccgtt | 240 |
| gcgatcaacg | gtatgagcaa | tggcattttt | gcccggttcg | gcacgtttca | tagtatcgcg | 300 |
| cactggtgcg | gcgaggatcc | ccccgtgcg | gctggtttcg | ctcaacgcca | acaatcgcgc | 360 |
| gaggtcatcc | tgatgcaaac | aaggacgagc | ggcgtcatgc | accaataccc | actgcgcgtc | 420 |
| gccagcggct | ttcagacctg | ccagcacgga | atcggcacgc | tcatcaccgc | catctacaac | 480 |

```
ggtgatttgc ggatgattcg ccagaggaag ttgtgcaaaa cggctatcgc caggacttat      540
ggcaatgacg acacgtttca cccggggatg cgccagcagc gcatgcaccg agtgttcaag      600
aatggtttga ttaccgattg agagatattg cttaggacat tccgtttgca ttcgacggcc      660
aaatccggcc gccggaacca cggcgcaaac atccaaatga gtggttgcca t               711

<210> SEQ ID NO 13
<211> LENGTH: 570
<212> TYPE: DNA
<213> ORGANISM: Bacillus subtilis
<220> FEATURE:
<221> NAME/KEY: CDS
<222> LOCATION: (1)...(567)

<400> SEQUENCE: 13 atg aag aaa atc gga att ttc gga ggc acg ttt gac cct ccg cat aat        48
Met Lys Lys Ile Gly Ile Phe Gly Gly Thr Phe Asp Pro Pro His Asn
 1               5                  10                  15 ggt cac ctc tta atg gcg aat gag gtg ctg tac cag gcg ggg ctt gat        96
Gly His Leu Leu Met Ala Asn Glu Val Leu Tyr Gln Ala Gly Leu Asp
             20                  25                  30 gaa att tgg ttt atg cct aat caa att ccg ccg cat aaa cag aac gaa       144
Glu Ile Trp Phe Met Pro Asn Gln Ile Pro Pro His Lys Gln Asn Glu
     35                  40                  45 gac tat acc gac agc ttt cat cgc gtg gaa atg cta aag ctt gca att       192
Asp Tyr Thr Asp Ser Phe His Arg Val Glu Met Leu Lys Leu Ala Ile
 50                  55                  60 caa tct aat ccg tcc ttt aag ctg gag ctt gtt gaa atg gaa aga gaa       240
Gln Ser Asn Pro Ser Phe Lys Leu Glu Leu Val Glu Met Glu Arg Glu
 65                  70                  75                  80 ggg cca tca tat acc ttt gat acc gtt tct tta ctg aag cag cgt tat       288
Gly Pro Ser Tyr Thr Phe Asp Thr Val Ser Leu Leu Lys Gln Arg Tyr
             85                  90                  95 cca aat gat cag ctg ttc ttt att atc ggc gct gat atg att gaa tat       336
Pro Asn Asp Gln Leu Phe Phe Ile Ile Gly Ala Asp Met Ile Glu Tyr
            100                 105                 110 ttg ccg aaa tgg tat aag ctg gac gag ctg ctg aac ctc att caa ttt       384
Leu Pro Lys Trp Tyr Lys Leu Asp Glu Leu Leu Asn Leu Ile Gln Phe
        115                 120                 125 att gga gta aag cgc ccc ggt ttt cat gtt gaa acc cct tat ccg ctt       432
Ile Gly Val Lys Arg Pro Gly Phe His Val Glu Thr Pro Tyr Pro Leu
    130                 135                 140 ctc ttt gca gac gtt ccg gaa ttt gag gta tca tca act atg ata agg       480
Leu Phe Ala Asp Val Pro Glu Phe Glu Val Ser Ser Thr Met Ile Arg
145                 150                 155                 160 gaa cgg ttt aaa agc aag aag ccc act gac tac tta atc cct gat aaa       528
Glu Arg Phe Lys Ser Lys Lys Pro Thr Asp Tyr Leu Ile Pro Asp Lys
                165                 170                 175 gtg aag aag tat gta gag gag aat ggt tta tat gaa tcg tga               570
Val Lys Lys Tyr Val Glu Glu Asn Gly Leu Tyr Glu Ser
            180                 185

<210> SEQ ID NO 14
<211> LENGTH: 189
<212> TYPE: PRT
<213> ORGANISM: Bacillus subtilis

<400> SEQUENCE: 14

Met Lys Lys Ile Gly Ile Phe Gly Gly Thr Phe Asp Pro Pro His Asn
 1               5                  10                  15

Gly His Leu Leu Met Ala Asn Glu Val Leu Tyr Gln Ala Gly Leu Asp
```

```
                    20                  25                  30
Glu Ile Trp Phe Met Pro Asn Gln Ile Pro Pro His Lys Gln Asn Glu
             35                  40                  45

Asp Tyr Thr Asp Ser Phe His Arg Val Glu Met Leu Lys Leu Ala Ile
         50                  55                  60

Gln Ser Asn Pro Ser Phe Lys Leu Glu Leu Val Glu Met Glu Arg Glu
     65                  70                  75                  80

Gly Pro Ser Tyr Thr Phe Asp Thr Val Ser Leu Leu Lys Gln Arg Tyr
                 85                  90                  95

Pro Asn Asp Gln Leu Phe Phe Ile Ile Gly Ala Asp Met Ile Glu Tyr
             100                 105                 110

Leu Pro Lys Trp Tyr Lys Leu Asp Glu Leu Leu Asn Leu Ile Gln Phe
         115                 120                 125

Ile Gly Val Lys Arg Pro Gly Phe His Val Glu Thr Pro Tyr Pro Leu
     130                 135                 140

Leu Phe Ala Asp Val Pro Glu Phe Glu Val Ser Ser Thr Met Ile Arg
145                 150                 155                 160

Glu Arg Phe Lys Ser Lys Pro Thr Asp Tyr Leu Ile Pro Asp Lys
                 165                 170                 175

Val Lys Lys Tyr Val Glu Glu Asn Gly Leu Tyr Glu Ser
             180                 185
```

<210> SEQ ID NO 15
<211> LENGTH: 570
<212> TYPE: DNA
<213> ORGANISM: Bacillus subtilis

<400> SEQUENCE: 15

```
tcacgattca tataaaccat tctcctctac atacttcttc actttatcag ggattaagta     60
gtcagtgggc ttcttgcttt taaaccgttc ccttatcata gttgatgata cctcaaattc    120
cggaacgtct gcaaagagaa gcggataagg ggtttcaaca tgaaaaccgg ggcgctttac    180
tccaataaat tgaatgaggt tcagcagctc gtccagctta taccatttcg gcaaatattc    240
aatcatatca gcgccgataa taaagaacag ctgatcattt ggataacgct gcttcagtaa    300
agaaacggta tcaaggtat atgatggccc ttctcttcc atttcaacaa gctccagctt    360
aaaggacgga ttagattgaa ttgcaagctt tagcatttcc acgcgatgaa agctgtcggt    420
atagtcttcg ttctgtttat gcggcggaat ttgattaggc ataaaccaaa tttcatcaag    480
ccccgcctgg tacagcacct cattcgccat taagaggtga ccattatgcg agggtcaaa    540
cgtgcctccg aaaattccga ttttcttcat                                    570
```

<210> SEQ ID NO 16
<211> LENGTH: 642
<212> TYPE: DNA
<213> ORGANISM: Escherichia coli
<220> FEATURE:
<221> NAME/KEY: CDS
<222> LOCATION: (1)...(639)

<400> SEQUENCE: 16

```
atg aaa tct tta cag gct ctg ttt ggc ggc acc ttt gat ccg gtg cac     48
Met Lys Ser Leu Gln Ala Leu Phe Gly Gly Thr Phe Asp Pro Val His
  1               5                  10                  15 tat ggt cat cta aaa ccc gtg gaa acg ctg gcg aat ttg att ggt ctg     96
Tyr Gly His Leu Lys Pro Val Glu Thr Leu Ala Asn Leu Ile Gly Leu
             20                  25                  30
```

-continued

```
acg cgg gtc aca atc atc cct aat aat gtt cct ccg cat cgt ccc cag      144
Thr Arg Val Thr Ile Ile Pro Asn Asn Val Pro Pro His Arg Pro Gln
         35                  40                  45 ccg gaa gcg aac agc gtg cag cgt aaa cac atg ctt gaa ctg gcg att      192
Pro Glu Ala Asn Ser Val Gln Arg Lys His Met Leu Glu Leu Ala Ile
 50                  55                  60 gcc gac aag cca tta ttt act ctt gat gaa cgc gag cta aag cgc aat      240
Ala Asp Lys Pro Leu Phe Thr Leu Asp Glu Arg Glu Leu Lys Arg Asn
 65                  70                  75                  80 gcc ccc tct tac act gcg caa aca ctg aaa gag tgg cgg cag gaa caa      288
Ala Pro Ser Tyr Thr Ala Gln Thr Leu Lys Glu Trp Arg Gln Glu Gln
                 85                  90                  95 gga ccg gac gtg ccg ctg gcg ttt att att ggt cag gat tca ctg ctg      336
Gly Pro Asp Val Pro Leu Ala Phe Ile Ile Gly Gln Asp Ser Leu Leu
            100                 105                 110 acc ttt ccg acc tgg tac gaa tac gaa acg ata ctc gac aat gca cat      384
Thr Phe Pro Thr Trp Tyr Glu Tyr Glu Thr Ile Leu Asp Asn Ala His
        115                 120                 125 ttg atc gtc tgt cgg cgt cca ggt tac cca ctt gaa atg gcg caa ccg      432
Leu Ile Val Cys Arg Arg Pro Gly Tyr Pro Leu Glu Met Ala Gln Pro
130                 135                 140 caa tac cag caa tgg ctg gaa gat cat ttg aca cat aac ccg gaa gat      480
Gln Tyr Gln Gln Trp Leu Glu Asp His Leu Thr His Asn Pro Glu Asp
145                 150                 155                 160 ctt cac ctt cag cct gcc ggt aaa att tat ctg gct gaa acg ccg tgg      528
Leu His Leu Gln Pro Ala Gly Lys Ile Tyr Leu Ala Glu Thr Pro Trp
                165                 170                 175 ttt aac atc tcg gcg acc atc atc cgc gaa cgt ttg caa aac ggt gaa      576
Phe Asn Ile Ser Ala Thr Ile Ile Arg Glu Arg Leu Gln Asn Gly Glu
            180                 185                 190 tca tgt gag gat tta ttg ccg gaa ccg gta ctg act tac att aac caa      624
Ser Cys Glu Asp Leu Leu Pro Glu Pro Val Leu Thr Tyr Ile Asn Gln
        195                 200                 205 caa ggc ttg tat cgc tga                                              642
Gln Gly Leu Tyr Arg
    210
```

<210> SEQ ID NO 17
<211> LENGTH: 213
<212> TYPE: PRT
<213> ORGANISM: Escherichia coli

<400> SEQUENCE: 17

```
Met Lys Ser Leu Gln Ala Leu Phe Gly Gly Thr Phe Asp Pro Val His
  1               5                  10                  15

Tyr Gly His Leu Lys Pro Val Glu Thr Leu Ala Asn Leu Ile Gly Leu
             20                  25                  30

Thr Arg Val Thr Ile Ile Pro Asn Asn Val Pro Pro His Arg Pro Gln
         35                  40                  45

Pro Glu Ala Asn Ser Val Gln Arg Lys His Met Leu Glu Leu Ala Ile
 50                  55                  60

Ala Asp Lys Pro Leu Phe Thr Leu Asp Glu Arg Glu Leu Lys Arg Asn
 65                  70                  75                  80

Ala Pro Ser Tyr Thr Ala Gln Thr Leu Lys Glu Trp Arg Gln Glu Gln
                 85                  90                  95

Gly Pro Asp Val Pro Leu Ala Phe Ile Ile Gly Gln Asp Ser Leu Leu
            100                 105                 110

Thr Phe Pro Thr Trp Tyr Glu Tyr Glu Thr Ile Leu Asp Asn Ala His
        115                 120                 125
```

```
Leu Ile Val Cys Arg Arg Pro Gly Tyr Pro Leu Glu Met Ala Gln Pro
    130                 135                 140

Gln Tyr Gln Gln Trp Leu Glu Asp His Leu Thr His Asn Pro Glu Asp
145                 150                 155                 160

Leu His Leu Gln Pro Ala Gly Lys Ile Tyr Leu Ala Glu Thr Pro Trp
                165                 170                 175

Phe Asn Ile Ser Ala Thr Ile Ile Arg Glu Arg Leu Gln Asn Gly Glu
            180                 185                 190

Ser Cys Glu Asp Leu Leu Pro Glu Pro Val Leu Thr Tyr Ile Asn Gln
        195                 200                 205

Gln Gly Leu Tyr Arg
    210

<210> SEQ ID NO 18
<211> LENGTH: 642
<212> TYPE: DNA
<213> ORGANISM: Escherichia coli

<400> SEQUENCE: 18
tcagcgatac aagccttgtt ggttaatgta agtcagtacc ggttccggca ataaatcctc      60
acatgattca ccgttttgca aacgttcgcg gatgatggtc gccgagatgt aaaccacgg     120 cgtttcagcc agataaattt taccggcagg ctgaaggtga agatcttccg ggttatgtgt    180
caaatgatct tccagccatt gctggtattg cggttgcgcc atttcaagtg ggtaacctgg    240
acgccgacag acgatcaaat gtgcattgtc gagtatcgtt tcgtattcgt accaggtcgg    300
aaaggtcagc agtgaatcct gaccaataat aaacgccagc ggcacgtccg gtccttgttc    360
ctgccgccac tctttcagtg tttgcgcagt gtaagagggg gcattgcgct ttagctcgcg    420
ttcatcaaga gtaaataatg gcttgtcggc aatcgccagt tcaagcatgt gtttacgctg    480
cacgctgttc gcttccggct ggggacgatg cggaggaaca ttattaggga tgattgtgac    540
ccgcgtcaga ccaatcaaat tcgccagcgt ttccacgggt tttagatgac catagtgcac    600
cggatcaaag gtgccgccaa acagagcctg taaagatttc at                       642

<210> SEQ ID NO 19
<211> LENGTH: 21
<212> TYPE: DNA
<213> ORGANISM: Artificial Sequence
<220> FEATURE:
<223> OTHER INFORMATION: primer for PCR

<400> SEQUENCE: 19
gtgttcgtgc tgacttgcac c                                               21

<210> SEQ ID NO 20
<211> LENGTH: 21
<212> TYPE: DNA
<213> ORGANISM: Artificial Sequence
<220> FEATURE:
<223> OTHER INFORMATION: primer for PCR

<400> SEQUENCE: 20
gaattatttc ctcccgttaa a                                               21

<210> SEQ ID NO 21
<211> LENGTH: 21
<212> TYPE: DNA
<213> ORGANISM: Artificial Sequence
<220> FEATURE:
```

<223> OTHER INFORMATION: primer for PCR

<400> SEQUENCE: 21
acaagtgatt gtaccaactg c                                           21

<210> SEQ ID NO 22
<211> LENGTH: 42
<212> TYPE: DNA
<213> ORGANISM: Artificial Sequence
<220> FEATURE:
<223> OTHER INFORMATION: primer for PCR

<400> SEQUENCE: 22
ggtgcaagtc agcacgaaca caatagttcg attgtcatag gc                    42

<210> SEQ ID NO 23
<211> LENGTH: 20
<212> TYPE: DNA
<213> ORGANISM: Artificial Sequence
<220> FEATURE:
<223> OTHER INFORMATION: primer for PCR

<400> SEQUENCE: 23
gcaaagggca agaaaaatga                                             20

<210> SEQ ID NO 24
<211> LENGTH: 41
<212> TYPE: DNA
<213> ORGANISM: Artificial Sequence
<220> FEATURE:
<223> OTHER INFORMATION: primer for PCR

<400> SEQUENCE: 24
ggtgcaagtc agcacgaaca cttggcaagt tactgatccc c                     41

<210> SEQ ID NO 25
<211> LENGTH: 42
<212> TYPE: DNA
<213> ORGANISM: Artificial Sequence
<220> FEATURE:
<223> OTHER INFORMATION: primer for PCR

<400> SEQUENCE: 25
tttaacggga ggaaataatt ctgctagact acatcgagaa gg                    42

<210> SEQ ID NO 26
<211> LENGTH: 21
<212> TYPE: DNA
<213> ORGANISM: Artificial Sequence
<220> FEATURE:
<223> OTHER INFORMATION: primer for PCR

<400> SEQUENCE: 26
gatactccac ggtacgagct g                                           21

<210> SEQ ID NO 27
<211> LENGTH: 41
<212> TYPE: DNA
<213> ORGANISM: Artificial Sequence
<220> FEATURE:
<223> OTHER INFORMATION: primer for PCR

<400> SEQUENCE: 27
tttaacggga ggaaataatt caggaaaaga tgtgggtttg g                     41

```
<210> SEQ ID NO 28
<211> LENGTH: 20
<212> TYPE: DNA
<213> ORGANISM: Artificial Sequence
<220> FEATURE:
<223> OTHER INFORMATION: primer for PCR

<400> SEQUENCE: 28
cttccatctc caataacggc                                              20
```